US011419645B2

(12) United States Patent
Stinson et al.

(10) Patent No.: US 11,419,645 B2
(45) Date of Patent: Aug. 23, 2022

(54) INTRAMEDULLARY FIXATION DEVICE WITH SHAPE LOCKING INTERFACE

(71) Applicants: University of British Columbia, Vancouver (CA); British Columbia Cancer Agency Branch, Vancouver (CA)

(72) Inventors: David Thomas Stinson, Woodinville, WA (US); Carly Anderson Thaler, Seattle, WA (US)

(73) Assignees: University of British Columbia, Vancouver (CA); British Columbia Cancer Agency Branch, Vancouver (CA)

( * ) Notice: Subject to any disclaimer, the term of this patent is extended or adjusted under 35 U.S.C. 154(b) by 191 days.

(21) Appl. No.: 16/340,067

(22) PCT Filed: Oct. 5, 2017

(86) PCT No.: PCT/US2017/055442
§ 371 (c)(1),
(2) Date: Apr. 5, 2019

(87) PCT Pub. No.: WO2018/067888
PCT Pub. Date: Apr. 12, 2018

(65) Prior Publication Data
US 2020/0054372 A1 Feb. 20, 2020

Related U.S. Application Data

(60) Provisional application No. 62/406,658, filed on Oct. 5, 2016.

(51) Int. Cl.
*A61B 17/72* (2006.01)

(52) U.S. Cl.
CPC ...... *A61B 17/7233* (2013.01); *A61B 17/7208* (2013.01)

(58) Field of Classification Search
CPC ............ A61B 17/7233; A61B 17/7208; A61B 17/7225
See application file for complete search history.

(56) References Cited

U.S. PATENT DOCUMENTS

| 4,706,659 A | 11/1987 | Matthews et al. |
| 5,108,397 A | 4/1992 | White |

(Continued)

FOREIGN PATENT DOCUMENTS

| AT | 509852 A4 | 12/2011 |
| CN | 2699846 Y | 5/2005 |

(Continued)

OTHER PUBLICATIONS

European Patent Office, "Extended European Search Report EP Application No. 17859233.3", from Foreign Counterpart to U.S. Appl. No. 16/340,067, dated Apr. 23, 2020, pp. 1 through 8, Published: EP.

(Continued)

*Primary Examiner* — Ellen C Hammond
(74) *Attorney, Agent, or Firm* — Fortem IP LLP; Mary Fox

(57) ABSTRACT

Implantable devices for fixation of curved bones such as the pelvic ring pubic symphysis and acetabulum, and methods for the use of the devices are disclosed. The implantable devices are convertible between a flexible state and a rigid state using a shape locking section. The implantable devices further include a main body and a distal bone interface. In a flexible state, the devices may be inserted along, and (Continued)

conform to a curved pathway, and in the rigid state, the devices may support the mechanical loads required to fixate a fracture.

26 Claims, 21 Drawing Sheets

(56) References Cited

U.S. PATENT DOCUMENTS

| | | |
|---|---|---|
| 5,167,665 A | 12/1992 | Mckinney |
| 5,234,435 A | 8/1993 | Seagrave, Jr. |
| D346,218 S | 4/1994 | White |
| 5,300,071 A | 4/1994 | Browner et al. |
| 5,336,224 A | 8/1994 | Selman |
| 5,527,309 A | 6/1996 | Shelton |
| 5,527,310 A | 6/1996 | Cole et al. |
| 5,593,407 A | 1/1997 | Reis |
| 5,601,550 A | 2/1997 | Esser |
| 5,649,925 A | 7/1997 | Barbera Alacreu |
| 5,879,352 A | 3/1999 | Filoso et al. |
| 5,944,719 A | 8/1999 | Leban |
| 6,340,362 B1 | 1/2002 | Pierer et al. |
| 6,368,326 B1 | 4/2002 | Dakin et al. |
| 7,258,692 B2 | 8/2007 | Thelen et al. |
| 7,410,483 B2 | 8/2008 | Danitz et al. |
| 7,625,395 B2 | 12/2009 | Muckter et al. |
| 7,632,277 B2 | 12/2009 | Woll et al. |
| 7,785,325 B1 | 8/2010 | Milbank |
| 7,846,162 B2 | 12/2010 | Nelson et al. |
| 8,043,347 B2 | 10/2011 | Jiang et al. |
| 8,128,626 B2 | 3/2012 | Justin |
| 8,128,627 B2 | 3/2012 | Justin et al. |
| 8,206,389 B2 | 6/2012 | Huebner et al. |
| 8,372,074 B2 | 2/2013 | Milbank |
| 8,409,257 B2 | 4/2013 | Edidin et al. |
| 8,439,916 B2 | 5/2013 | Coati et al. |
| 8,632,543 B2 | 1/2014 | Metzinger et al. |
| 8,961,516 B2 | 2/2015 | Nelson et al. |
| 9,060,809 B2 | 6/2015 | Tipirneni et al. |
| 9,144,506 B2 | 9/2015 | Phelps |
| 9,155,574 B2 | 10/2015 | Saravia et al. |
| 9,482,260 B1 | 11/2016 | Krause |
| 9,498,264 B2 | 11/2016 | Harshman et al. |
| 9,839,435 B2 | 12/2017 | Meek et al. |
| 2002/0032444 A1 | 3/2002 | Mische |
| 2002/0087161 A1 | 7/2002 | Randall et al. |
| 2002/0198527 A1 | 12/2002 | Muckter |
| 2003/0078582 A1 | 4/2003 | Heggeness |
| 2003/0181982 A1 | 9/2003 | Kuslich |
| 2003/0187449 A1 | 10/2003 | McCleary et al. |
| 2004/0024409 A1 | 2/2004 | Sand et al. |
| 2004/0102778 A1 | 5/2004 | Huebner et al. |
| 2004/0215191 A1 | 10/2004 | Kitchen |
| 2005/0055023 A1 | 3/2005 | Sohngen et al. |
| 2005/0085819 A1 | 4/2005 | Ellis et al. |
| 2005/0154390 A1 | 7/2005 | Biedermann et al. |
| 2005/0165401 A1 | 7/2005 | Pack |
| 2006/0074421 A1 | 4/2006 | Bickley et al. |
| 2006/0264950 A1 | 11/2006 | Nelson et al. |
| 2007/0083204 A1 | 4/2007 | Sidebotham |
| 2007/0162132 A1 | 7/2007 | Messerli |
| 2007/0208364 A1 | 9/2007 | Smith et al. |
| 2007/0233111 A1 | 10/2007 | Orbay et al. |
| 2008/0051786 A1 | 2/2008 | Jensen |
| 2008/0058722 A1 | 3/2008 | Von Oepen et al. |
| 2008/0077133 A1 | 3/2008 | Schulze |
| 2008/0077154 A1 | 3/2008 | Edwards et al. |
| 2008/0108989 A1 | 5/2008 | Parsell et al. |
| 2008/0161805 A1 | 7/2008 | Saravia et al. |
| 2008/0195145 A1 | 8/2008 | Bonutti et al. |
| 2008/0234676 A1 | 9/2008 | Schulze et al. |
| 2008/0249628 A1 | 10/2008 | Altarac et al. |
| 2008/0269745 A1 | 10/2008 | Justin |
| 2008/0287951 A1 | 11/2008 | Stoneburner et al. |
| 2008/0294163 A1 | 11/2008 | Chou et al. |
| 2008/0294164 A1 | 11/2008 | Frank et al. |
| 2008/0319455 A1 | 12/2008 | Harris et al. |
| 2009/0024174 A1 | 1/2009 | Stark |
| 2009/0048672 A1 | 2/2009 | Essenmacher |
| 2009/0062797 A1 | 3/2009 | Huebner et al. |
| 2009/0192512 A1 | 7/2009 | Sommers |
| 2009/0216232 A1 | 8/2009 | Buford, III et al. |
| 2010/0023010 A1 | 1/2010 | Nelson et al. |
| 2010/0076503 A1 | 3/2010 | Beyar et al. |
| 2010/0185290 A1 | 7/2010 | Compton et al. |
| 2010/0217333 A1 | 8/2010 | McShane et al. |
| 2010/0249832 A1 | 9/2010 | Stopek et al. |
| 2010/0249838 A1 | 9/2010 | Stopek et al. |
| 2010/0249854 A1 | 9/2010 | Thomas et al. |
| 2010/0249944 A1 | 9/2010 | Thomas et al. |
| 2010/0262239 A1 | 10/2010 | Boyden et al. |
| 2010/0286692 A1 | 11/2010 | Greenhalgh et al. |
| 2010/0298893 A1 | 11/2010 | Stucki |
| 2010/0318137 A1 | 12/2010 | Stucki et al. |
| 2010/0331842 A1 | 12/2010 | Milbank |
| 2011/0015684 A1 | 1/2011 | Belcheva et al. |
| 2011/0028974 A1 | 2/2011 | Chemello |
| 2011/0040282 A1 | 2/2011 | Uihlein |
| 2011/0046746 A1 | 2/2011 | Rabiner et al. |
| 2011/0087227 A1 | 4/2011 | Mazur et al. |
| 2011/0098757 A1 | 4/2011 | Schelling |
| 2011/0098816 A1 | 4/2011 | Jacob et al. |
| 2011/0098817 A1 | 4/2011 | Eckhardt et al. |
| 2011/0119815 A1 | 5/2011 | Paulson et al. |
| 2011/0144643 A1 | 6/2011 | Lorenz et al. |
| 2011/0144645 A1 | 6/2011 | Saravia et al. |
| 2011/0144703 A1 | 6/2011 | Krause et al. |
| 2011/0153454 A1 | 6/2011 | Dunn et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196435 A1 | 8/2011 | Forsell |
| 2011/0230966 A1 | 9/2011 | Trieu |
| 2011/0238181 A1 | 9/2011 | Trieu |
| 2011/0264229 A1 | 10/2011 | Donner |
| 2011/0288598 A1 | 11/2011 | Moed et al. |
| 2011/0306975 A1 | 12/2011 | Kaikkonen et al. |
| 2011/0319944 A1 | 12/2011 | Borodic |
| 2012/0010617 A1 | 1/2012 | Maza |
| 2012/0065638 A1 | 3/2012 | Moore |
| 2012/0078252 A1 | 3/2012 | Huebner et al. |
| 2012/0078311 A1 | 3/2012 | Huebner et al. |
| 2012/0083847 A1 | 4/2012 | Huebner et al. |
| 2012/0083895 A1 | 4/2012 | Conway et al. |
| 2012/0101533 A1 | 4/2012 | Purcell et al. |
| 2012/0101576 A1 | 4/2012 | Dewey et al. |
| 2013/0006145 A1 | 1/2013 | Toomey et al. |
| 2013/0006245 A1 | 1/2013 | Stoneburner et al. |
| 2013/0012942 A1 | 1/2013 | Nelson et al. |
| 2013/0131678 A1 | 5/2013 | Dahners |
| 2013/0144348 A1 | 6/2013 | Schwappach |
| 2013/0325007 A1 | 12/2013 | Beyar et al. |
| 2014/0114312 A1 | 4/2014 | Krause |
| 2014/0309636 A1 | 10/2014 | Meek et al. |
| 2014/0358146 A1 | 12/2014 | Meek et al. |
| 2015/0157370 A1 | 6/2015 | Gross |
| 2015/0257800 A1 | 9/2015 | Harshman et al. |
| 2017/0014170 A1 | 1/2017 | Fallin et al. |
| 2017/0020585 A1 | 1/2017 | Harshman et al. |
| 2017/0238977 A1 | 8/2017 | Harshman et al. |
| 2019/0231401 A1 | 8/2019 | Harshman et al. |
| 2019/0282280 A1 | 9/2019 | Harshman et al. |
| 2021/0220027 A1 | 7/2021 | Harshman et al. |

FOREIGN PATENT DOCUMENTS

| | | |
|---|---|---|
| CN | 101633119 A | 1/2010 |
| CN | 101636119 A | 1/2010 |
| CN | 102793579 A | 11/2012 |
| CN | 104203132 A | 12/2014 |
| CN | 104203132 B | 8/2017 |
| CN | 107106217 A | 8/2017 |
| EP | 2779928 A1 | 9/2014 |
| EP | 3326558 A1 | 5/2018 |

(56) References Cited

FOREIGN PATENT DOCUMENTS

| | | |
|---|---|---|
| EP | 3206608 | 7/2018 |
| WO | 2007009123 A2 | 1/2007 |
| WO | 2008116175 A2 | 9/2008 |
| WO | 2008120877 A1 | 10/2008 |
| WO | 2009143374 A2 | 11/2009 |
| WO | 2010124230 A1 | 10/2010 |
| WO | 2011067668 A1 | 6/2011 |
| WO | 2011119815 A2 | 9/2011 |
| WO | 2011153454 A2 | 12/2011 |
| WO | 2012107913 A2 | 8/2012 |
| WO | 2013063145 A1 | 5/2013 |
| WO | 2013071432 A1 | 5/2013 |
| WO | 2015134750 A1 | 9/2015 |
| WO | 2016061173 A1 | 4/2016 |
| WO | 2018067888 A1 | 4/2018 |
| WO | 2020077457 A1 | 4/2020 |

OTHER PUBLICATIONS

U.S. Patent and Trademark Office, "Office Action", U.S. Appl. No. 15/952,093, dated Mar. 6, 2020, pp. 1-71, Published: US.
International Searching Authority, "International Search Report and Written Opinion from PCT Application No. PCT/CA2019/051471", dated Feb. 5, 2020, pp. 1-14, Published: WO.
U.S. Patent and Trademark Office, "Final Office Action", U.S. Appl. No. 15/952,093, dated Sep. 25, 2020, pp. 1 through 19, Published: US.
U.S. Patent and Trademark Office, "Notice of Allowance", U.S. Appl. No. 14/357,917, dated Jul. 26, 2017, pp. 1-5, Published: US.
U.S. Patent and Trademark Office, "Notice of Allowance", U.S. Appl. No. 15/519,148, dated Feb. 13, 2019, pp. 1-42, Published: US.
U.S. Patent and Trademark Office, "Office Action for U.S. Appl. No. 15/285,811 dated Oct. 18, 2018", pp. 1-39, Published in: US.
U.S. Patent and Trademark Office, "Office Action", U.S. Appl. No. 14/300,752, dated Apr. 5, 2016, pp. 1-16, Published: US.
U.S. Patent and Trademark Office, "Office Action", U.S. Appl. No. 14/300,752, dated Aug. 8, 2017, pp. 1-16, Published: US.
U.S. Patent and Trademark Office, "Office Action", U.S. Appl. No. 14/300,752, dated Oct. 20, 2014, pp. 1-14, Published: US.
U.S. Patent and Trademark Office, "Office Action", U.S. Appl. No. 14/357,917, dated Apr. 18, 2016, pp. 1-10, Published: US.
U.S. Patent and Trademark Office, "Office Action", U.S. Appl. No. 14/727,576, dated Oct. 16, 2015, pp. 1-14, Published: US.
U.S. Patent and Trademark Office, "Office Action", U.S. Appl. No. 14/727,576, dated Apr. 28, 2016, pp. 1-15, Published: US.
U.S. Patent and Trademark Office, "Office Action", U.S. Appl. No. 15/519,148, dated Jul. 26, 2018, pp. 1-38, Published: US.
U.S. Patent and Trademark Office, "Restriction Requirement", U.S. Appl. No. 14/357,917, dated Jan. 21, 2016, pp. 1-6, Published: US.
U.S. Patent and Trademark Office, "Restriction Requirement", U.S. Appl. No. 14/727,576, dated Jul. 23, 2015. pp. 1-10, Published: US.
U.S. Patent and Trademark Office, "Restriction Requirement", U.S. Appl. No. 15/285,811, dated Mar. 30, 2018, pp. 1-7, Published: US.
U.S. Pat. No. 7,273,482, (withdrawn).
Vaidya, R., et al., "Complications of Anterior Subcutaneous Internal Fixation for Unstable Pelvis Fractures: A Multicenter Study," Clinical Orthopaedicsand Related Research, Aug. 2012, pp. 1-8 vol. 470, No. 8, Springer.
U.S. Patent and Trademark Office, "Notice of Allowance", U.S. Appl. No. 15/285,811, dated Mar. 25, 2019, pp. 1-11, Published: US.
China National Intellectual Property Administration, "Notice of Decision of Granting Patent Right for Invention from CN Application No. 201580061380.2 dated Sep. 10, 2019", from Foreign Counterpart to U.S. Appl. No. 15/519,148, pp. 1-5, Published: CN.
European Patent Office, "Communication pursuant to Article 94(3) from EP Application No. 15850096.7", from Foreign Counterpart to U.S. Appl. No. 15/519,148, dated Oct. 15, 2019, pp. 1-5, Published: EP.
U.S. Patent and Trademark Office, "Restriction Requirement", U.S. Appl. No. 15/952,093, dated Nov. 29, 2019, pp. 1-8, Published: US.
U.S. Patent and Trademark Office, "Office Action", U.S. Appl. No. 16/384,758, dated Jul. 24, 2020, pp. 1 through 69, Published: US.
U.S. Patent and Trademark Office, "Office Action", U.S. Appl. No. 16/414,435, dated Jul. 14, 2020, pp. 1 through 62, Published: US.
International Bureau, "International Preliminary Report on Patentability from PCT Application No. PCT/CA2019/051471", from Foreign Counterpart to U.S. Appl. No. 17/286,388, dated Apr. 29, 2021, pp. 1 through 9, Published: WO.
U.S. Patent and Trademark Office, "Final Office Action", U.S. Appl. No. 16/414,435, dated Mar. 22, 2021, pp. 1 through 26, Published: US.
U.S. Patent and Trademark Office, "Office Action", U.S. Appl. No. 15/952,093, dated May 13, 2021, pp. 1 through 25, Published: US.
"UT Southwest Medical Surgeons Market Pelvic Fracture Device," accessed at http://www.texasbusiness.com/ut-southwest-medical-surgeons-market-pelvic-fracture-device-cms-4418, Apr. 22, 2011, pp. 1-5, Texas Business.com.
Australian Government IP Australia, "Examination report No. 1 for standard patent application from AU Application No. 2015333623 dated Sep. 26, 2017", from Foreign Counterpart to U.S. Appl. No. 15/519,148, filed Sep. 26, 2017, pp. 1-4, Published: AU.
Australian Government IP Australia, "Notice of acceptance for patent application from AU Application No. 2015333623 dated Jul. 20, 2018", from Foreign Counterpart to PCT Application No. PCT/US2015/055441, Jul. 20, 2018, pp. 1-3, Published: AU.
Australian Government IP Australia, "Notice of Acceptance from AU Application No. 2012339536 dated Jan. 28, 2016", from Foreign Counterpart to PCT Application No. PCT/CA2012/050808, Jan. 28, 2016, pp. 1-3, Published: AU.
Australian Government IP Australia, "Patent Examination Report No. 1 from AU Application No. 2012339536 dated Jan. 23, 2015", from Foreign Counterpart to U.S. Appl. No. 14/357,917, filed Jan. 23, 2015, pp. 1-5, Published: AU.
Australian Government IP Australia, "Patent Examination Report No. 2 from AU Application No. 2012339536 dated Oct. 16, 2015", from Foreign Counterpart to U.S. Appl. No. 14/357,917, filed Oct. 16, 2015, pp. 1-6, Published: AU.
Barry et al., "Flexible intramedullary nails for fractures in children", Aspects of Current Management, Sep. 2004, pp. 1-7, vol. 86-B, No. 7, British Editorial Society of Bone and Joint Surgery.
Canadian Intellectual Property Office, "Office Action from CA Application No. 2,855,752 dated Feb. 3, 2017", from Foreign Counterpart to U.S. Appl. No. 14/357,917, filed Feb. 3, 2017, pp. 1-4, Published: CA.
Canadian Intellectual Property Office, "Office Action from CA Application No. 2,855,752 dated Mar. 9, 2018", from Foreign Counterpart to U.S. Appl. No. 14/357,917, filed Mar. 9, 2018, pp. 1-5, Published: CA.
Canadian Intellectual Property Office, "Office Action from CA Application No. 2,855,752 dated Oct. 28, 2015", from Foreign Counterpart to U.S. Appl. No. 14/357,917, filed Oct. 28, 2015, pp. 1-4, Published: CA.
Canadian Intellectual Property Office, "Office Action from CA Application No. 2,964,370 dated Jan. 24, 2019", from Foreign Counterpart to U.S. Appl. No. 15/519,148, filed Jan. 24, 2019, pp. 1-6, Published: CA.
Canadian Intellectual Property Office, "Office Action from CA Application No. 2,964,370 dated May 4, 2018", from Foreign Counterpart to U.S. Appl. No. 15/519,148, filed May 4, 2018, pp. 1-7, Published: CA.
Canadian Intellectual Property Office, "Office Action from CA Application No. 2978697 dated Oct. 19, 2018", from Foreign Counterpart to PCT Application No. PCT/US2015/018969, Oct. 19, 2018, pp. 1-4, Published: CA.
Cheung, et al., "A new halo-pelvic apparatus", Spine, (2003), vol. 28, No. 3, pp. 1-8.
China National Intellectual Property Office, "Office Action from CN Application No. 201580061380.2 dated Dec. 21, 2018", from Foreign Counterpart to U.S. Appl. No. 15/519,148, filed Dec. 21, 2018, pp. 1-18, Published: CN.

(56) References Cited

OTHER PUBLICATIONS

European Patent Office, "Communication pursuant to Article 94(3) from EP Application No. 12849005.9 dated Jun. 2, 2016", from Foreign Counterpart to U.S. Appl. No. 14/357,917, filed Jun. 2, 2016, pp. 1-4, Published: EP.
European Patent Office, "Communication pursuant to Article 94(3) from EP Application No. 12849005.9 dated Nov. 25, 2016", from Foreign Counterpart to PCT Application No. PCT/CA2012/050808, Nov. 25, 2016, pp. 1-4, Published: EP.
European Patent Office, "Communication under Rule 71(3) from EP Application No. 12849005.9 dated Jul. 25, 2017", from Foreign Counterpart to U.S. Appl. No. 14/357,917, filed Jul. 25, 2017, pp. 1-6, Published: EP.
European Patent Office, "Extended European Search Report from EP Application No. 12849005.9 dated Jun. 15, 2015", from Foreign Counterpart to PCT Application No. PCT/CA2012/050808, Jun. 15, 2015, pp. 1-6, Published: EP.
European Patent Office, "Extended European Search Report from EP Application No. 15850096.7 dated Jun. 8, 2018", from Foreign Counterpart to U.S. Appl. No. 15/519,148, filed Jun. 8, 2018, pp. 1-12, Published: EP.
European Patent Office, "Extended European Search Report from EP Application No. 17207050.0 dated Apr. 20, 2018", from Foreign Counterpart to U.S. Appl. No. 14/357,917, filed Apr. 20, 2018, pp. 1-6, Published: EP.
Ganz, et al., "Surgical dislocation of the adult hip", The Journal of Bone and Joint Surgery (Br), Nov. 2004, pp. 1119-1124, vol. 83-B, No. 8, British Editorial Society of Bone and Joint Surgery.
Griffin et al., "Vertically Unstable Pelvic Fractures Fixed with Percutaneous Iliosacral Screws: Does Posterior Injury Pattern Prediction Fixation Failure?", Journal of Orthopedic Trauma, Jan. 2006, pp. 399-405, vol. 17, No. 6, Lippincott Williams, and Wilkins, Inc.
International Bureau, "International Preliminary Report on Patentability from PCT Application No. PCT/CA2012/050808 dated May 20, 2014", from Foreign Counterpart to U.S. Appl. No. 14/357,917, filed May 20, 2014, pp. 1-6, Published: Switzerland.
International Searching Authority, "International Search Report and Written Opinion from PCT Application No. PCT/CA2012/050808 dated Feb. 26, 2013", from Foreign Counterpart to U.S. Appl. No. 14/357,917, filed Feb. 26, 2013, pp. 1-10, Published: WO.
International Searching Authority, "International Search Report and Written Opinion from PCT Application No. PCT/US2015/055441 dated Feb. 9, 2016", from Foreign Counterpart to U.S. Appl. No. 15/519,148, filed Feb. 9, 2016, pp. 1-15, Published: WO.
International Searching Authority, "International Search Report and Written Opinion from PCT Application No. PCT/US2017/055442 dated Dec. 11, 2017", Dec. 11, 2017, pp. 1-14, Published: US.
International Searching Authority, "International Search Report and Written Opinion of the International Searching Authority from PCT Application No. PCT/US15/18969 dated May 27, 2015", from Foreign Counterpart to U.S. Appl. No. 14/727,576, filed May 27, 2015, pp. 1-6, Published: US.
Japanese Patent Office, "Decision to Grant from JP Application No. 2017519539 dated Jul. 31, 2018", from Foreign Counterpart to PCT Application No. PCT/US2015/055441, Jul. 31, 2018, pp. 1-3, Published: JP.
Japanese Patent Office, "Office Action from JP Application No. 2017519539 dated Jan. 10, 2018", from Foreign Counterpart to PCT Application No. PCT/US2015/055441, Jan. 10, 2018, pp. 1-6, Published: JP.
Miller et al., "Variations in Sacral Morphology and Implications for Iliosacral Screw Fixation", Journal of the American Academy of Orthopaedic Surgeons, Jan. 2012, pp. 8-16, vol. 20, No. 1, American Academy of Orthopaedic Surgeons.
Novick, "Pelvic Fractures/Acetabular Fractures", Hospital for Special Surgery, Mar. 30, 2006, pp. 1-9, HSS.edu.
Novick, "Pelvic Fractures/Fractures of the Acetabulum", Hospital for Special Surgery, Mar. 30, 2006, pp. 1-10.
Starr et al., "Superior Pubic Ramus Fractures Fixed With Percutaneous Screws: What Predicts Fixation Failure?", Journal of Orthopaedic Trauma, Feb. 2008, pp. 81-87, vol. 22, No. 2, Lippincott Williams and Wilkins.
Starr, "Fractures of the Pelvic Ring," in Rockwood & Green's Fractures in Adults 6th Edition, Chapter—41, accessed on Feb. 4, 2014, pp. 1-40, Lippincott Williams & Wilkins.
State Intellectual Property Office of P.R. China, "Notification on Grant of the Patent Right for Invention from CN Application No. 2012800661802 dated Apr. 28, 2017", from Foreign Counterpart to PCT Application No. PCT/CA2012/050808, Apr. 28, 2017, pp. 1-3, Published: CN.
State Intellectual Property Office, P.R. China, "Office Action from CN Application No. 201280066180.2 dated Aug. 3, 2016", from Foreign Counterpart to U.S. Appl. No. 14/357,917, filed Aug. 3, 2016, pp. 1-6, Published: CN.
State Intellectual Property Office, P.R. China, "Office Action from CN Application No. 201280066180.2 dated Dec. 28, 2015", from Foreign Counterpart to U.S. Appl. No. 14/357,917, filed Dec. 28, 2015, pp. 1-7, Published: CN.
State Intellectual Property Office, P.R. China, "Search Report from CN Application No. 201280066180.2 dated Aug. 10, 2016", from Foreign Counterpart to U.S. Appl. No. 14/357,917, filed Aug. 10, 2016, pp. 1-3, Published: CN.
State Intellectual Property Office, P.R. China, "Third Office Action from CN Application No. 201280066180.2 dated Jan. 5, 2017", from Foreign Counterpart to U.S. Appl. No. 14/357,917, filed Jan. 5, 2017, pp. 1-4, Published: CN.
U.S. Patent and Trademark Office, "Advisory Action", U.S. Appl. No. 14/300,752, dated Feb. 16, 2017, pp. 1-3, Published: US.
U.S. Patent and Trademark Office, "Advisory Action", U.S. Appl. No. 14/300,752, dated Oct. 7, 2015, pp. 1-3, Published: US.
U.S. Patent and Trademark Office, "Final Office Action", U.S. Appl. No. 14/300,752, dated Jan. 12, 2018, pp. 1-18, Published: US.
U.S. Patent and Trademark Office, "Final Office Action", U.S. Appl. No. 14/300,752, dated May 28, 15, pp. 1-14, Published: US.
U.S. Patent and Trademark Office, "Final Office Action", U.S. Appl. No. 14/300,752, dated Nov. 3, 2016, pp. 1-15, Published: US.
U.S. Patent and Trademark Office, "Final Office Action", U.S. Appl. No. 14/357,917, dated Sep. 6, 2016, pp. 1-11, Published: US.
U.S. Patent and Trademark Office, "Interview Summary" U.S. Appl. No. 14/727,576, dated Feb. 17, 2016, pp. 1-4, Published: US.
U.S. Patent and Trademark Office, "Interview Summary", U.S. Appl. No. 14/727,576, dated Jun. 14, 2016, pp. 1-3, Published: US.
U.S. Patent and Trademark Office, "Notice of Allowance" U.S. Appl. No. 14/727,576, dated Jul. 19, 2016, pp. 1-8, Published: US.
U.S. Patent and Trademark Office, "Advisory Action", U.S. Appl. No. 16/414,435, dated Aug. 24, 2021, pp. 1 through 4, Published: US.
European Patent Office, "Communication pursuant to Article 94(3) from U.S. Appl. No. 14/357,917 dated Jul. 22, 2019", from Foreign Counterpart to U.S. Appl. No. 14/357,917, pp. 1-5, Published: EP.
Canadian Intellectual Property Office, "Notice of Allowance from CA Application No. 2964370", from Foreign Counterpart to U.S. Appl. No. 15/519,148, dated Dec. 13, 2019, p. 1, Published: CA.
U.S. Patent and Trademark Office, "Notice of Allowance", U.S. Appl. No. 16/384,758, dated Dec. 2, 2020, pp. 1 through 21, Published: US.
U.S. Patent and Trademark Office, "Advisory Action", U.S. Appl. No. 15/952,093, dated Jan. 13, 2021, pp. 1 through 6, Published: US.
Canadian Intellectual Property Office, "Office Action from CA Application No. 2855752 dated Jun. 17, 2019", from Foreign Counterpart to U.S. Appl. No. 14/357,917, pp. 1-3, Published: CA.
International Bureau, "International Preliminary Report on Patentability from PCT Application No. PCT/US2017/055442 dated Apr. 18, 2019", from Foreign Counterpart to U.S. Appl. No. 16/340,067, pp. 1-8, Published: WO.
European Patent Office, "Communication pursuant to Article 94(3) EPC from EP Application No. 15850096.7", from Foreign Counterpart to U.S. Appl. No. 15/519,148, dated Sep. 21, 2020, pp. 1 through 4, Published: EP.

(56) References Cited

OTHER PUBLICATIONS

European Patent Office, "Communication pursuant to Article 94(3) EPC from EP Application No. 17207050.0", from Foreign Counterpart to U.S. Appl. No. 14/357,917, dated Aug. 26, 2020, pp. 1 through 3, Published: EP.

European Patent Office, "Communication pursuant to Article 94(3) EPC from EP Application No. 15850096.7", from Foreign Counterpart to U.S. Appl. No. 15/519,148, dated Oct. 5, 2021, pp. 1 through 5, Published: EP.

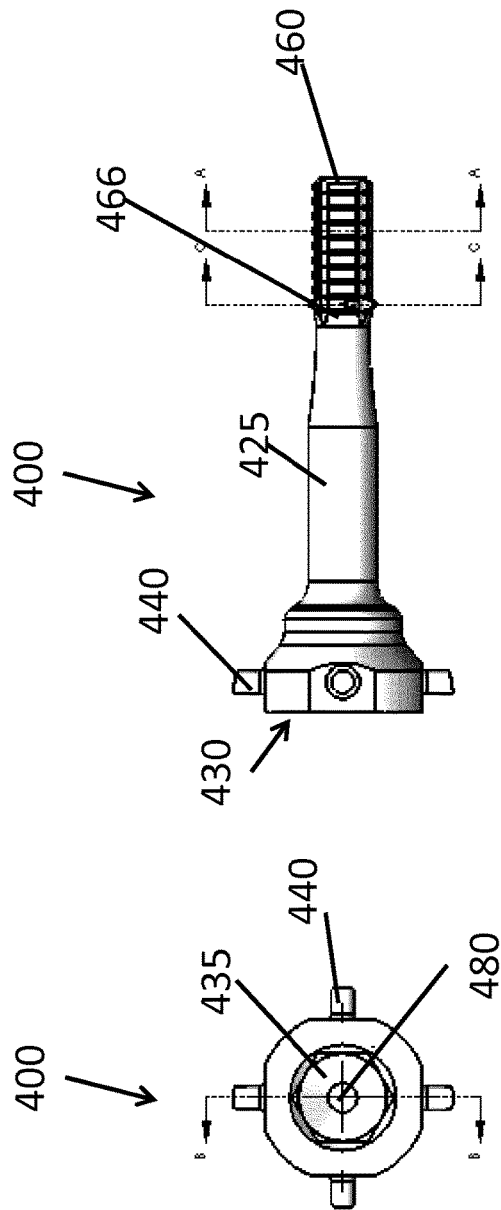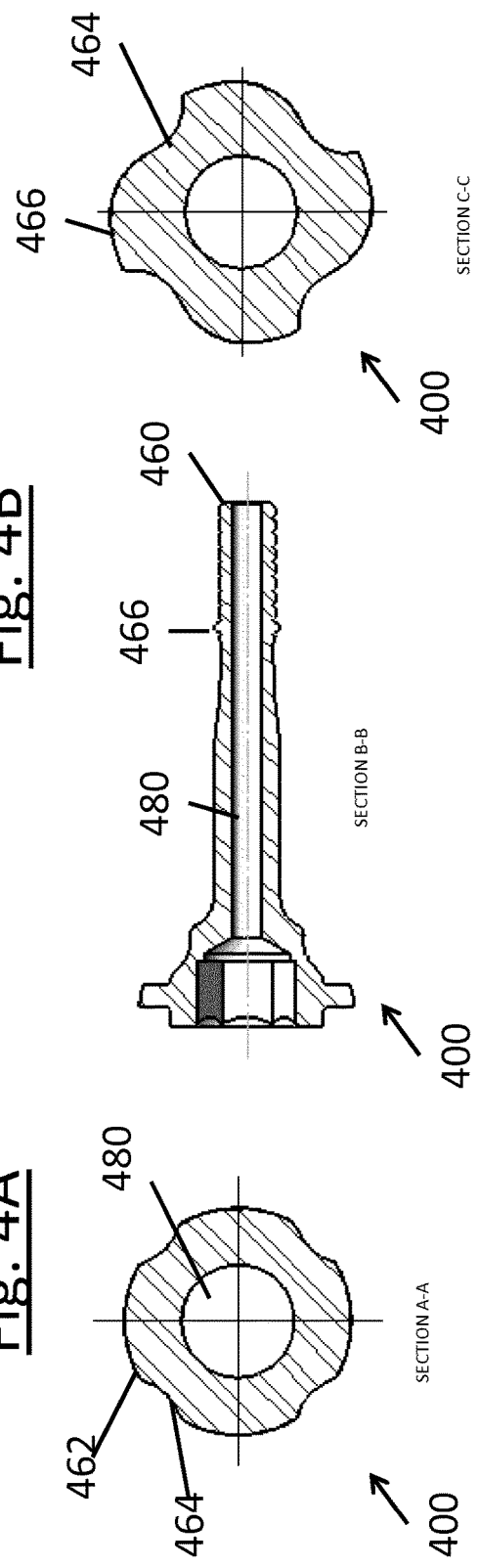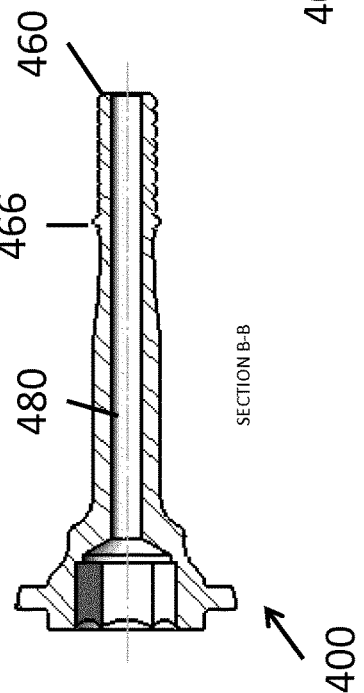

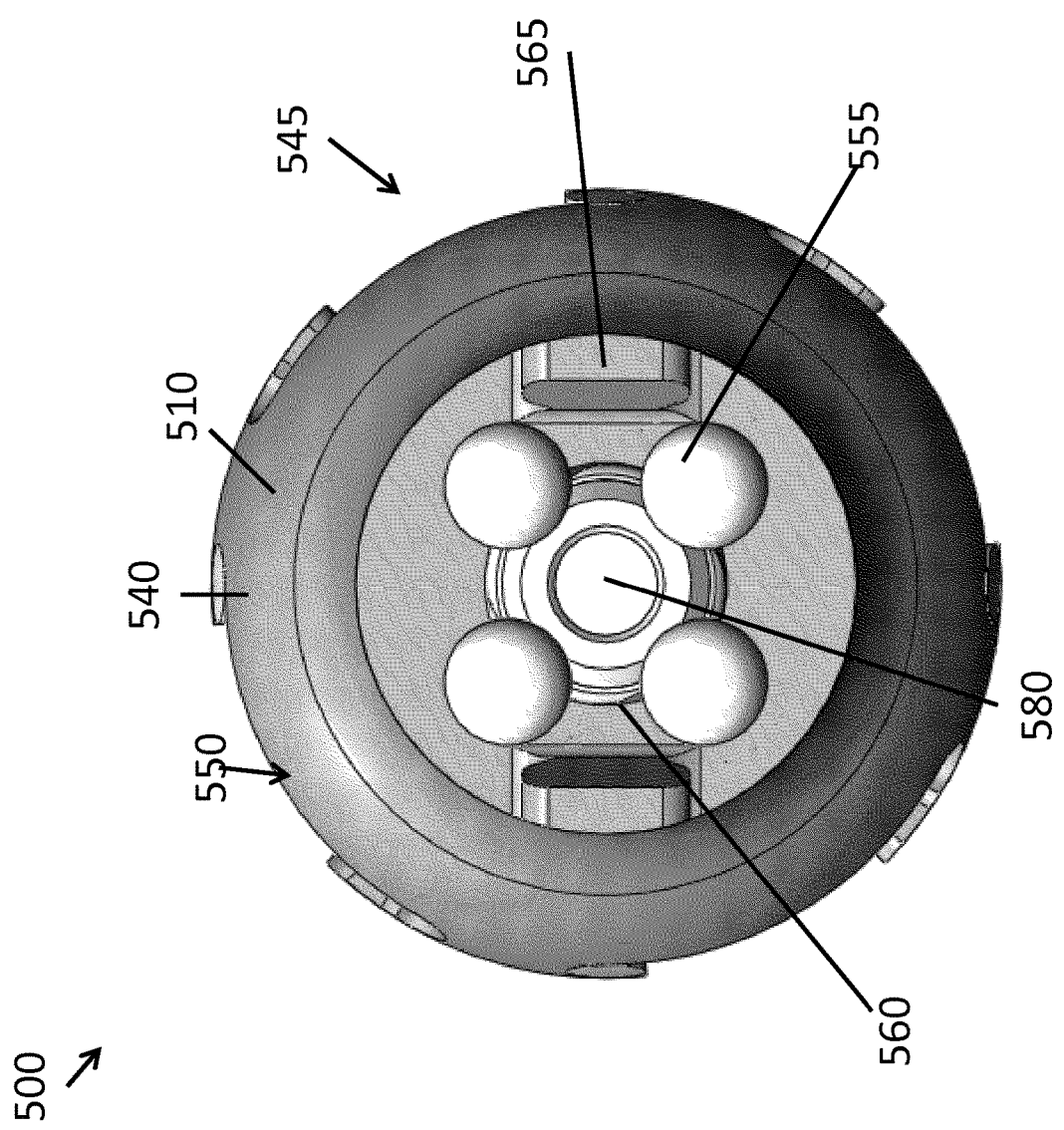

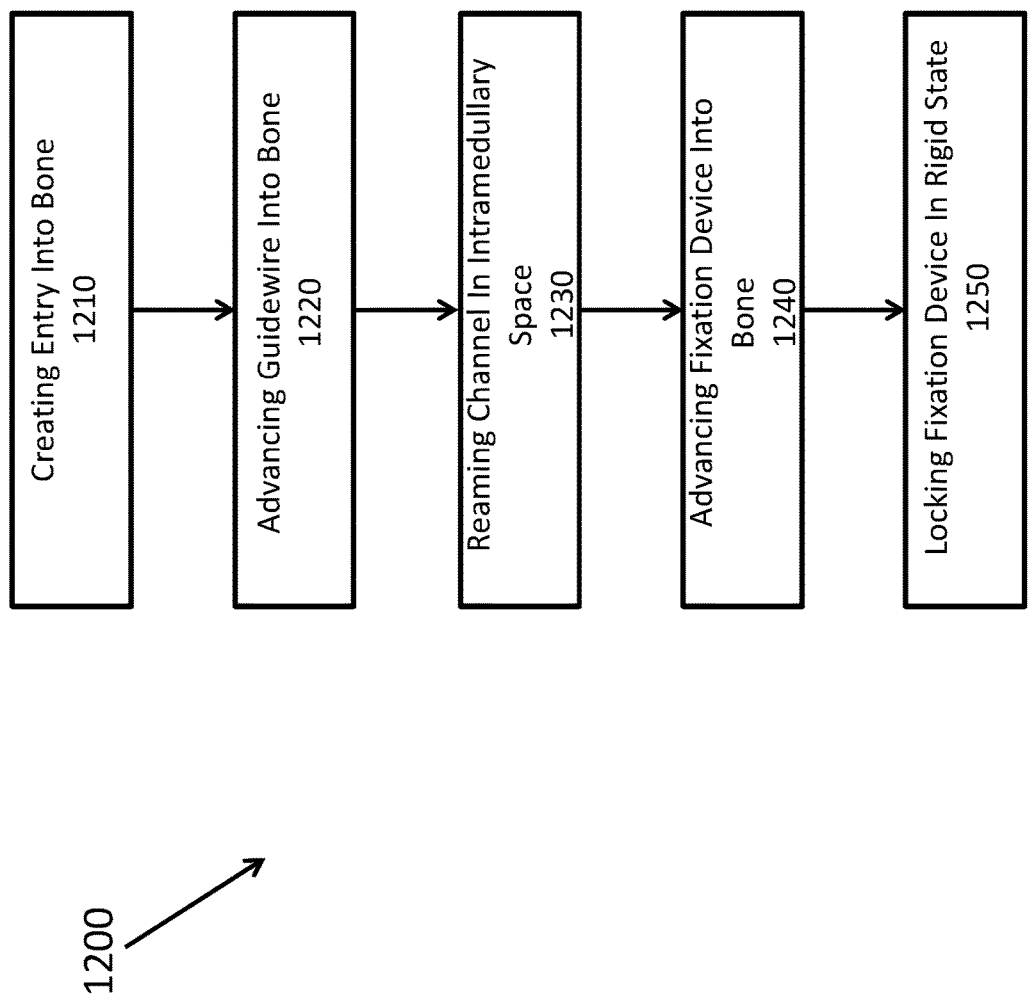

INTRAMEDULLARY FIXATION DEVICE WITH SHAPE LOCKING INTERFACE

This application claims priority to International Patent Application No. PCT/US2017/055442 filed on Oct. 5, 2017, which claims priority to U.S. Provisional Patent Application No. 62/404,658 filed on Oct. 5, 2016.

BACKGROUND

The following description is provided to assist the understanding of the reader. None of the information provided or references cited is admitted to be prior art.

Bone fractures may occur in straight bones, such as the femur, or in curved bones, such as pelvic bones. Repairing a bone fracture generally involves two steps: fracture reduction and fracture fixation. Reduction is the step of reducing the fracture by minimizing the distance between the bone fragments and aligning the bones anatomically to minimize deformity after healing. Both surgical and nonsurgical reduction methods exist. Fixation is the step of holding the bone fracture fragments mechanically stable and in close proximity to each other to promote bone healing which may take several weeks or more, depending on the type of fracture, type of bone and the general health of the patient suffering the injury.

Fixing bone fracture fragments in a mechanically stable manner to eliminate motion across the fracture site also minimizes pain when patients apply weight across the fracture during everyday activities like sitting or walking. Fixation of bone fractures may be accomplished by either internal or external fixation. Internal fixation is defined by mechanically fixing the bone fracture fragments with implanted devices. Examples of internal fixation include bone screws inserted within the bone across the fracture site and bone plates which are applied to the surface of the bone across the fracture site. Bone plates are typically attached to healthy bone using two or more bone screws.

External fixation is defined by methods and devices which mechanically fix the bone fracture fragments with devices or methods external to the body. The traditional uses of a splint or cast are examples of external fixation of a fractured bone. An example of an invasive external fixation device uses long screws that are inserted into bone on each side of the fracture. In pelvic fracture work the use of external skeletal fixation is common and involves placing long threaded pins into the iliac bones and then connecting them with an external frame. These screws are connected to a frame which is located outside the body.

Invasiveness of both fracture reduction and fixation steps varies depending on the devices and/or methods used. Invasive open reduction typically involves surgically dissecting to allow access the bone fracture. Dissection is performed through the skin, fat, and muscle layers, while avoiding injury to adjacent structures such as nerves, major blood vessels, and organs. Once dissection has been completed, the fracture may be reduced prior to definitive fixation and provisionally held using surgical clamps or other methods. Non-invasive closed reduction is typically performed by applying force to the patient's skin surface at different locations and/or to apply traction to a leg, to reduce the fracture. Minimally invasive reduction techniques minimize the surgical dissection area by reducing the size of the surgical wound and by directly pushing on the bone with various long handled tools through the minimal surgical wound. Invasive open fixation typically involves surgically dissecting to allow access to sufficient areas of healthy bone so that fixation devices such as surgical plates can be attached directly to the bone surface to fix the fracture site. Minimally invasive closed fixation typically involves insertion of a device such as a bone screw or intramedullary rod (or nail) within the bone through a small incision in the skin, fat, and muscle layers.

Minimally invasive reduction and fixation are typically used to repair long bone injuries such as the femur. One example is an intramedullary rod, also known as an intramedullary nail (IM nail), inter-locking nail or Küntschner nail. Intramedullary nails in the femur and tibia are load sharing devices and can well resist large bending and shearing forces, thereby allowing patients to leave hospital and manage with crutches in a short time.

The mechanical strength of bone fixation is determined by both the strength of the implant and strength of the implant's attachment to healthy bone. The mechanical forces applied across the fracture during the healing process can include shear, compression, tension (tensile), torsion, static loading and dynamic loading. In bones with complex curvature such as bones of the pelvis or of the spine, straight intramedullary fixation devices have limitations. Bone curvature limits the mechanical strength of attaching a straight intramedullary fixation device within healthy bone tissue. In pelvic and acetabular fracture fixation, an example of a straight intramedullary device is a commonly used cannulated bone screw. These screws must be limited in length and diameter because they are a straight device in a curved tunnel. If too long they will penetrate the bone and could injure important soft tissues. However, such screws may not offer secure fixation due to their low tensile pull out forces in cortical cancellous and/or osteoporotic bone during the healing process. Also, the diameter of the straight intramedullary screw, when in a curved bone, is significantly smaller than the thickness of the cancellous bone layer between the two outer cortical bone layers. Since the cancellous bone is significantly weaker than cortical bone (and can have significantly compromised strength in the case of osteoporotic bone) straight intramedullary screws may allow for the bone fragments to move relative to each other due to inadequate vertical shear holding force of cancellous bone. Plates normally act, mechanically, as tension band plates, neutralization plates or compression plates. Often a single plate will perform more than one of these mechanical functions, but since the plates are attached to the bone, the use of plates requires invasive open surgery to expose the bone. The plates are inherently weak because they have to be designed to be thin and have notches in them so that they can be bent to fit the curves of the pelvis. Invasive open surgery can result in increased blood loss, increased risk of infection and increased healing time compared to minimally invasive methods.

SUMMARY

Difficult mechanical fixation issues associated with fixation of curved bones such as are found in the pelvic ring and around the acetabulum, may be minimized or eliminated by using implantable devices that may be convertible between a flexible and a rigid state. These devices may include a proximal shape locking interface, a main body, and a distal bone interface. In a flexible state, the device may be inserted inside, and conform to a curved pathway, and in the rigid state, the device may support the tensile and vertical shear mechanical loads required to fix fractured bone segments. A fixation system may include an intramedullary fixation device, a guide wire, a reamer, and an extraction tool.

Methods of use may include usages of an intramedullary fixation device for fixation of pelvic ring and acetabular fractures, intramedullary guide wire placement within curved bone, intramedullary fixation device implantation over a guide wire, intramedullary fixation device attachment to bone at implant distal end, intramedullary fixation device attachment to bone at proximal end, and in some embodiments device conversion between flexible and rigid states using the proximal shape locking interface. In an embodiment, the body includes a plurality of individual segments having a mechanical engagement structure for non-rigidly interlocking the individual segments together. The segments have a plurality of channels or apertures arranged to generally form two or more lumens in the flexible body when the segments are in non-rigid mechanical engagement. The individual segments may move relative to each other in a first and a second orthogonal plane relative to the main axis. The fixation device may have a torque transmission member positioned substantially on the proximal end and a bone engagement feature positioned substantially on the distal end. One or more fibers extend through the lumens such that the fibers may provide a fixed shape to the flexible body when the fibers are fixed into position. The shape locking interface of the intramedullary fixation device is configured to selectively restrain the one or more fibers so as to selectively place the intramedullary fixation device into a rigid or flexible state.

In another embodiment, there is a method of fixing a reduced bone fracture in a curved bone. The method involving creating an entry into a curved bone, advancing a guidewire through an intramedullary space to a position distal to a reduced bone fracture, reaming a channel in the intramedullary space along the length of the guidewire, advancing an intramedullary fixation device through the channel and locking the intramedullary fixation device in place.

BRIEF DESCRIPTION OF THE FIGURES

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

FIGS. 4A-4F depict various views of an inner compression member of a shape locking section in accordance with an illustrative embodiment.

FIGS. 5A and 5B depict end views of a distal end of a shape locking section in an unlocked state in accordance with an illustrative embodiment.

FIG. 12 depicts a flow diagram for a method of fixing a reduced bone fragment in accordance with an illustrative embodiment.

DETAILED DESCRIPTION

Figure 1A:
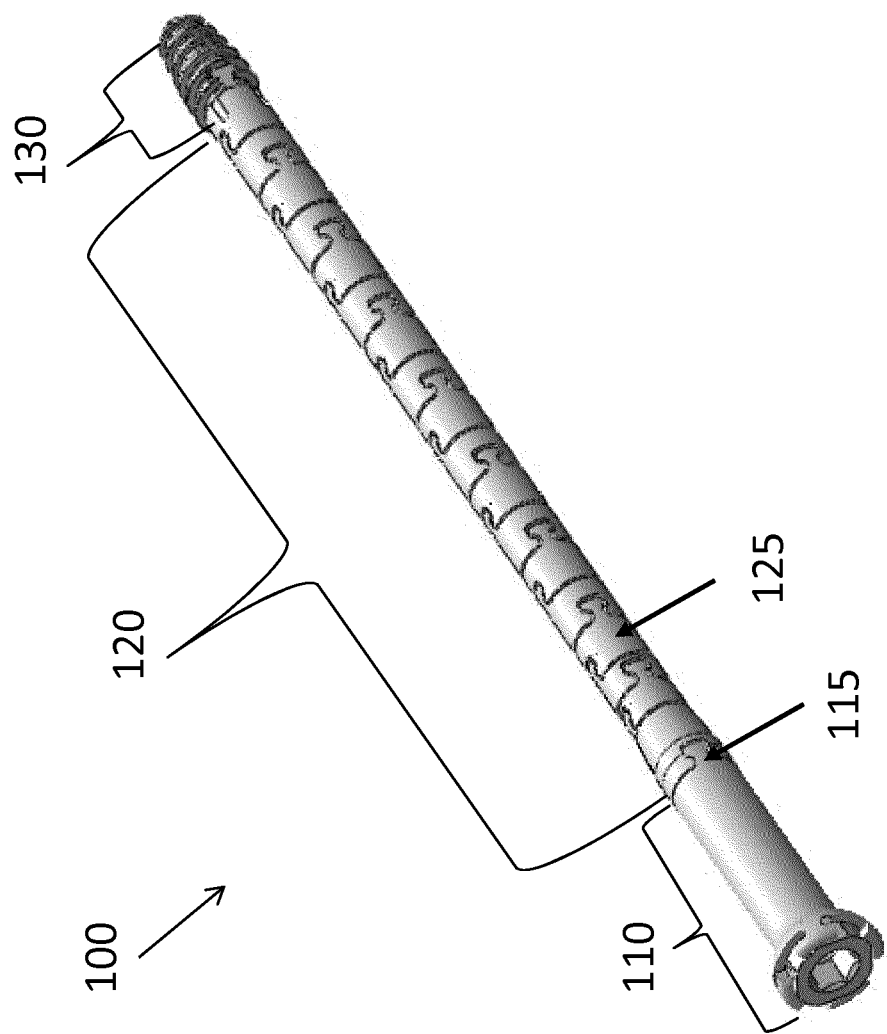
FIG. 1A depicts an isometric view of an intramedullary fixation device in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein are various embodiments for the fixation of fractured or broken bones. The systems, apparatuses, and methods described herein may be used on long and straight bones, but are designed specifically to treat curved bones. Curved bones may be generally straight with a section having a curve or arc length, generally curved without a distinguishable straight segment, or a combination of the two. Curved bones or non-linear bones include the zygoma, mandible (jaw bone), clavicle, scapula (the hemipelvis of the upper limb), ribs, spine, talus and calcaneus. The device may also have some applications in pediatric long bones.

In the discussion of the various systems, devices, and methods herein, references and orientation are made to facilitate the understanding of the described embodiment. The term "proximal" as used herein means the side or end of a device that tends to be the closest to the physician or operator when using the described embodiment. Alternatively, "proximal" may refer to the side or end of an embodiment that is the last to enter a patient body. The term "distal" refers to the end or side of the embodiment that is furthest away from the physician or operator. The term distal may alternatively mean the end or side of the embodiment that is first to enter the patient body. Several embodiments also make reference to a general axis. This axis is an imaginary axis based on the shape of some of the embodiments of the device and refers to the long axis of the embodiments having one dimension (of height, length or width) clearly longer or greater than the other two dimensions. The dimension which is the greatest is the dimension to which the general axis runs parallel. Note the general axis may not be a straight line, and may be curved or follow a tortuous path, so long as the axis is generally thought of as running parallel to the embodiment. Parallel may also include superimposed in the same line, whether straight or curved.

Described herein is an intramedullary fixation device with an adaptable or alterable shape capable of deployment within a bone or boney structure while having a flexible or non-rigid form, then adapting to an inflexible or rigid form after deployment. The intramedullary fixation device may revert to a flexible or non-rigid form subsequent to deployment for either further adjustment or removal from the bone or boney structure. Other embodiments are sufficiently flexible to be inserted along a curved path and sufficiently rigid after implantation without requiring a conversion step. The intramedullary fixation device with adaptable or alterable shape shall also simply be referred to herein as the device, support device or the apparatus.

In various embodiments, the device has a proximal end, a shape locking section (also referred to herein as a shape locking interface), a distal end, and an intermediate section. The device may be formed from a group of segments arranged in an end to end fashion, where each segment has a generally standardized shape. In various embodiments, the device may be flexible in two planes orthogonal to the general axis. In some embodiments, the device may be flexible in more than two planes orthogonal to the general axis. In some embodiments the standardized shape of each segment may include a generally cylindrical body having a first end and a second end. The first end may have a protrusion extending from the cylindrical body, and that protrusion may be formed or shaped so as to engage an aperture or receptacle shaped generally to receive the protrusion in a generally male to female arrangement. The cylindrical body may have one male end and one female end at the first or second ends. Alternatively the cylindrical body may have two male ends or two female ends. When the cylindrical bodies are lined up to form the device, the arrangement can be made so male ends are adjacent to and engage into female ends. The male and female connection maybe such that the adjacent segments do not separate from each other when moved relative to the other in at least one plane.

In various embodiments, the device may have a series of cylindrical bodies arranged in an end to end fashion with a male to female mechanical arrangement. In some embodiments the generally cylindrical body segments may have holes or apertures running parallel to the general axis. The holes may form one or more lumens in the device when the segments are generally lined up. In various embodiments, one or more fibers may be threaded through the holes in the segments, so that fibers extend from one end of the device to the other through the holes in the segments. In various embodiments the holes are lined up to form lumens through the device, so as to not crimp, impede or otherwise damage the fibers.

In various embodiments, the fibers may be affixed to the most distal segment and protrude from the most proximal segment so as to engage a shape locking section or interface. As discussed further herein, the shape locking section is configured to selectively lock the fibers that protrude from the most proximal segment in place, thereby changing the intramedullary fixation device from a flexible state to a rigid state or vice versa. In various embodiments, the fibers may be manipulated to fix the segments into a rigid or inflexible curved shape. In some embodiments, the fibers may subsequently be altered to return the device into a flexible or non-rigid shape. In various embodiments, the device may be advanced distally or retracted proximally while the device is either flexible or rigid. In some embodiments, the fibers may be cables, wires, rods or similar structures. The fibers may be made of biocompatible metal (for example, stainless steel, titanium or nitinol), alloys, polymers, biosorbable materials, ceramics, glass, carbon fiber or any combination of these materials. Additional materials are provided and/or described herein.

In various embodiments, the shape locking section is capable of converting the flexible configuration of the device into a rigid or inflexible configuration. In some embodiments, the shape locking interface may have an outer housing and an inner compression member. The outer housing may serve as one jaw of a clamping mechanism for the fibers which may be threaded through the shape locking section. The outer shell may also serve as a retaining member for the proximal section via an external thread. In some embodiments, the inner compression member is actuated to press the fibers feeding through the shape locking section against the outer housing. In some embodiments, the actuation of the inner compression member may comprise a rotation within the outer housing. In some embodiments, the actuation of the inner compression member may comprise longitudinal movement along the general axis of the outer housing with or without rotation within the outer housing. In some embodiments, the inner compression member may include cylindrical cuts, gear teeth, or other components designed to increase friction with the fibers and thereby better grip the fibers. As such, the inner compression member can selectively cause an interference fit between the outer housing, the fibers, and the inner compression member. The resulting interference fit between the various components causes the fibers to be locked into whatever position they were in when the force was applied.

In some embodiments, the shape of the device is facilitated by a guidewire or guide pin used to make an initial entry into the intramedullary space of the bone to be treated. The guidewire used may be one having a particular geometry to facilitate creating the desired shaped path in a curved intramedullary space. The device may be inserted over the guide wire or guide pin and traverse the length of the guide wire. The device including the shape locking interface may have a central aperture or hollow core through which the guide wire or guide pin may extend. While the device traverses the length of the guide wire, it follows the curvature of the guide wire and maintains that curvature during and after deployment. The fibers may be used to lock the individual segments in place relative to each other once the desired shape is acquired. The guide wire may be a flexible or stiff wire, a guide pin or other device having similarly useful characteristics to make the initial entry into a bone, and able to bear the device tracking over it. It is not essential that the guide wire be so robust that the device cannot alter the shape of the guide wire if desired.

In some embodiments, the proximal section of the device may contain one or more segments. The segments of the proximal section may have any of the features described herein and attributed to any segment, or may possess any of the following additional features. In various embodiments, the proximal section may serve as a proximal bone interface to anchor the proximal end of the device to the exterior bone surface. In some embodiments this may be an individual or singular component. In some embodiments the anchoring may be done by a set of components that together form an exterior surface that contacts the cortical bone at the proximal end of the device. In some embodiments, the proximal section may have an interior surface that mates with the rest of the support device. The mating of the proximal section and the bone may provide for transferring load from the bone to the device. The load path begins in the bone, passes into the proximal end of the device, through the device, and along to the distal end, and back into the bone (this assumes a fracture with heavily fragmented bone that cannot be compressed at the fracture site). Alternatively, if the bone can be compressed at the fracture, the load path is shared, passing through the bone in compression, and through the device in tension. In some embodiments the proximal section may have a bone interface like internal threads. The internal threads may fit over some external threads of a shape locking device, or of the intermediate section, or of the rest of the support device.

In some embodiments the distal section of the device may have one or more bone interface elements used to mechanically engage the bone. The distal section may anchor the distal end of the support device into a fixed position in the bone and prevent the distal end from moving.

In some embodiments the device may also have a polymer sleeve to help provide an atraumatic surface between the intramedullary fixation device and the bone.

In the various embodiments described herein, the intramedullary fixation device may be composed from a polymer, a metal, an alloy, or a combination thereof, which may be biocompatible. For example, the fracture stabilization device can be formed from titanium or a titanium alloy. Other suitable metals may include stainless steel, cobalt-chromium alloys, and tantalum. In some embodiments, metal alloys having shape memory capability, such as nickel titanium or spring stainless steel alloys, may also be used. In some embodiments, the fracture stabilization device can be formed from a suitable polymer including non-degradable polymers, such as polyetheretherketone (PEEK) and polyethylene (PE), as well as modified versions of these materials (for example, PEEK+calcium phosphates and PE+vitamin E, metal coatings, or surface texturing). Additional non limiting polymers may include; polyether-block co-polyamide polymers, copolyester elastomers, thermoset polymers, polyolefins (e.g., polypropylene or polyethylene, including high density polyethylene (HDPEs), low-density polyethylene (LDPEs), and ultrahigh molecular weight polyethylene (UHMWPE)), polytetrafluoroethylene, ethylene vinyl acetate, polyamides, polyimides, polyurethanes, polyvinyl chloride (PVC), fluoropolymers (e.g., fluorinated ethylene propylene, perfluoroalkoxy (PEA) polymer, polyvinylidene fluoride, etc.), polyetheretherketones (PEEKs), PEEK-carbon fiber composites, polyetherketoneketones (PEKKs), poly(methylmethacrylate) (PMMA), polysulfone (PSU), epoxy resins, and silicones. Additionally starch based polymers may be used.

Additional materials may include carbon and polyaramid structures, glass or fiberglass derivatives, ceramic materials, and artificial biocompatible protein derivatives (recombinant derived collagen). In other embodiments, the fracture stabilization device may be made of a metal and/or alloy segments with a polymer shell, or a sandwich style and coaxial extrusion composition of any number of layers of any of the materials listed herein. Various layers may be bonded to each other to provide for single layer composition of metal(s), alloys, and/or polymers. In another embodiment, a polymer core may be used with a metal and/or metal alloy shell, such as a wire or ribbon braid.

Furthermore, at least a portion of the device may be treated or coated with a calcium material, such as calcium deposits, calcium phosphate coatings, calcium sulfates, modified calcium salts such as magnesium, strontium and/or silicon substituted calcium phosphates, RGD sequences, collagen, and combinations thereof in order to enhance a strength of bone ingrowth, on-growth, and/or through-growth between the segments or other portions of the fracture stabilization device.

In some embodiments, the device as described herein may be used in a procedure to promote fixation of a fractured bone. In some embodiments, a method of fixing a fractured or broken bone may utilize any one or more of the steps such as creating a surgical incision in a patient to gain access to a bone surface, creating a hole in the bone, inserting a guide wire into the bone, navigating the guidewire along a curved path within the bone, feeding a flexible reamer over the guide wire, creating a channel for the support device, removing the reamer, advancing the device into the bone, adjusting the shape of the device, fixing the shape of the device using a shape locking section as described herein, and securing the device in the bone.

In some embodiments there may be one or more additional steps such as observing the movement of the guide wire, reamer or device into the bone, threading one or more sections of the device into the bone, securing the shape of the device through the shape locking section, rotating the device, applying torque to the device, applying torque to a section or segment of the support device.

In some instances, it becomes necessary to remove a bone fixation device from a patient. The device of the present disclosure may be removed following a series of steps similar to, but not necessarily opposite of the implanting steps. In some embodiments, the device may be removed from the bone by: exposing the shape locking section, returning the flexibility of the support feature, and removing the device from the bone.

In various embodiments, removal of the device may entail one or more additional steps, such as exposing the proximal end for manipulation, disengaging the proximal end from the shape locking section, actuating the shape locking section (or element), withdrawing the device, retracting any retractable bone engagement features, rotating the device, applying proximally directed force on the device or any of its sections and/or segments. Other embodiments may not use or require the shape locking section to be unlocked prior to removal.

FIG. 1A depicts an isometric view of an intramedullary fixation device 100 in accordance with an illustrative embodiment. Intramedullary fixation device 100 includes a shape locking section 110, a main body 120, and a bone engagement feature 130. Shape locking section 110 is at a proximal end of intramedullary fixation device and is connected to main body 120 by a connection 115. In an embodiment, connection 115 may be a tab and slot configuration or any other suitable connection as known to those of skill in the art. Main body 120 includes a plurality of individual segments 125 that each have a mechanical engagement structure for non-rigidly interlocking respective individual segments 125 together. Segments 125 have a plurality of channels or apertures arranged to generally form two or more lumens in main body 120 when segments 125 are in non-rigid mechanical engagement. Individual segments 125 may move relative to each other in a first and a second orthogonal plane relative to the main axis. One or more fibers extend through the lumens such that the fibers provide a fixed shape to main body 120 when the fibers are fixed into position by shape locking section 110. Main body 120 is connected to bone engagement feature 130 at a distal end. Bone engagement feature 130 includes a mechanism for engaging and becoming affixed to a bone to aid in holding intramedullary fixation device 100 in place upon implantation.

Figure 1B:
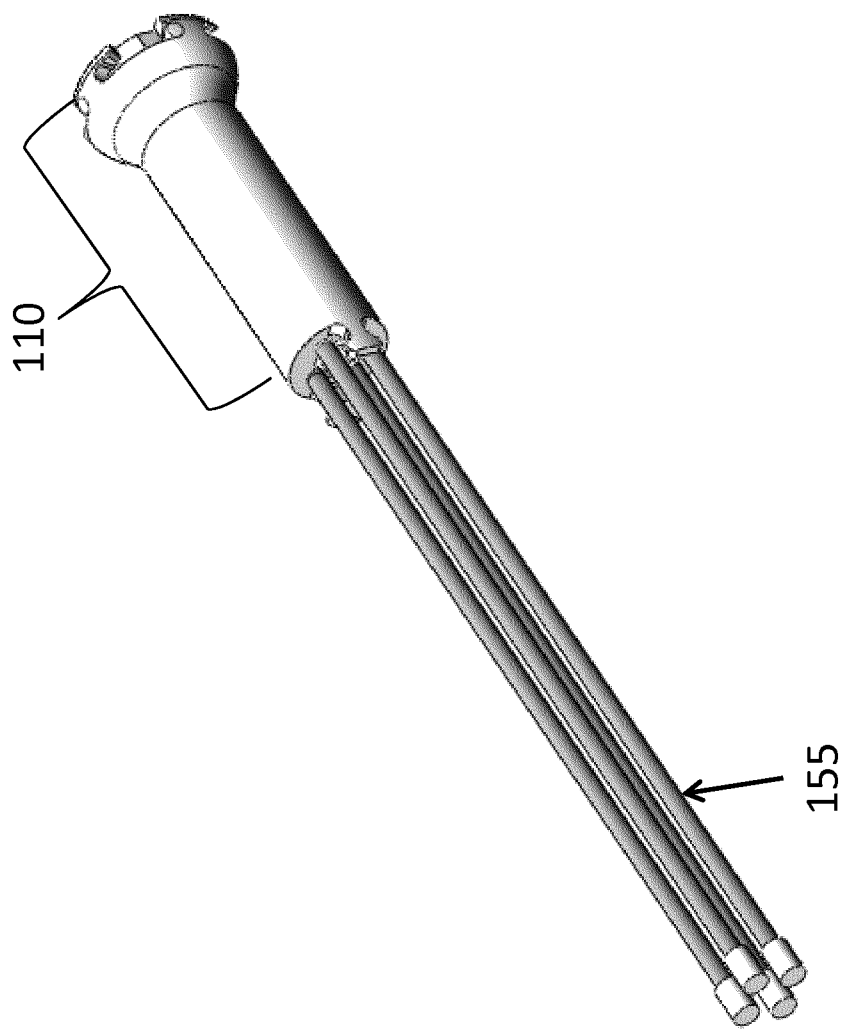
FIG. 1B depicts an isometric view of a shape locking section and fibers of an intramedullary fixation device in accordance with an illustrative embodiment.

FIG. 1B depicts an isometric view of shape locking section 110 and fibers 155 of an intramedullary fixation device in accordance with an illustrative embodiment. Fibers 155 extend partially shape locking section 110 through a distal end of shape locking section 110. Fibers 155 further extend through individual segments 125 of main body 125 (which have been omitted from FIG. 1B to better illustrate the relationship of fibers 155 to shape locking section 110).

Figure 2A:
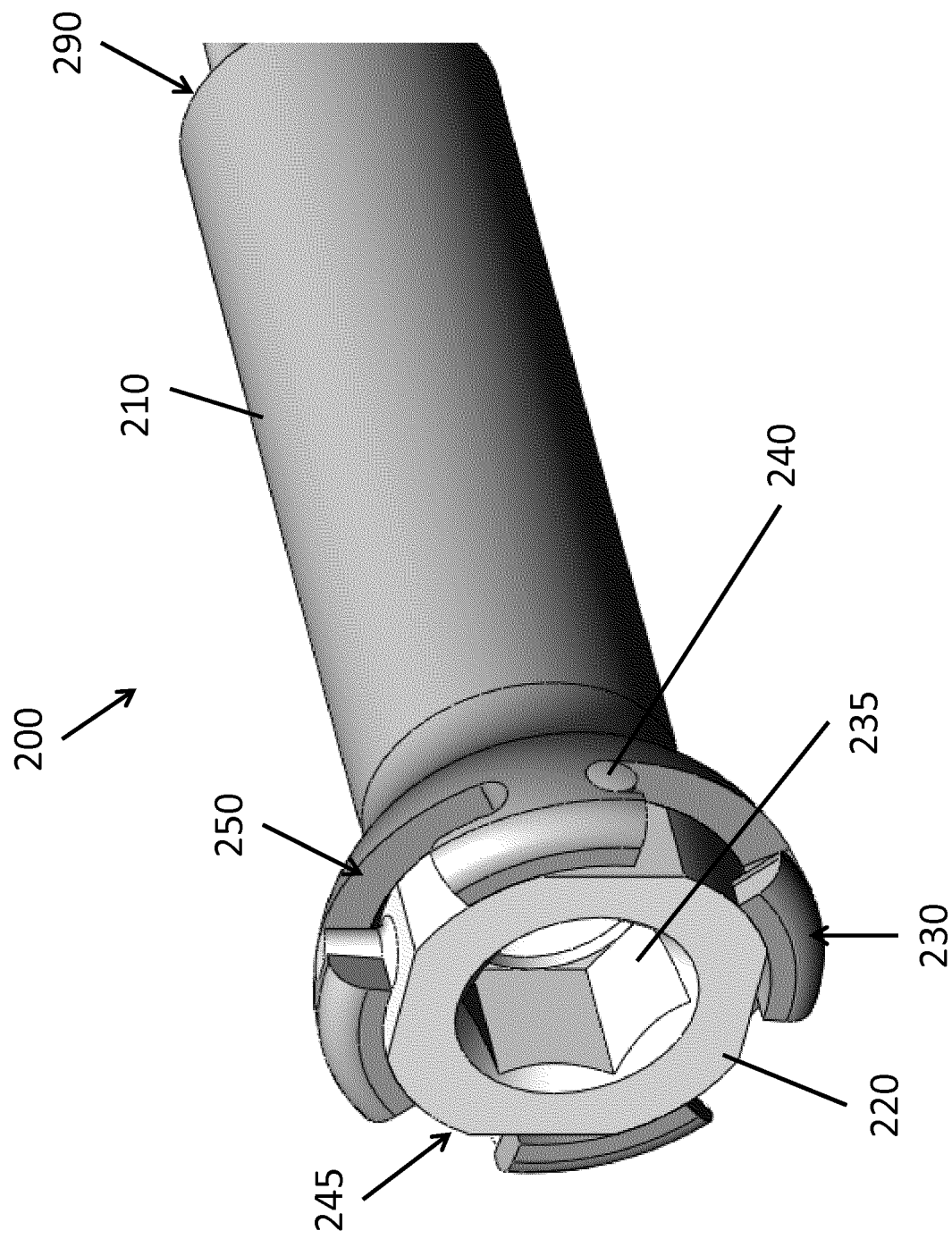
FIGS. 2A and 2B depict isometric views of a shape locking section of an intramedullary fixation device in an unlocked state in accordance with an illustrative embodiment.
Figure 2B:
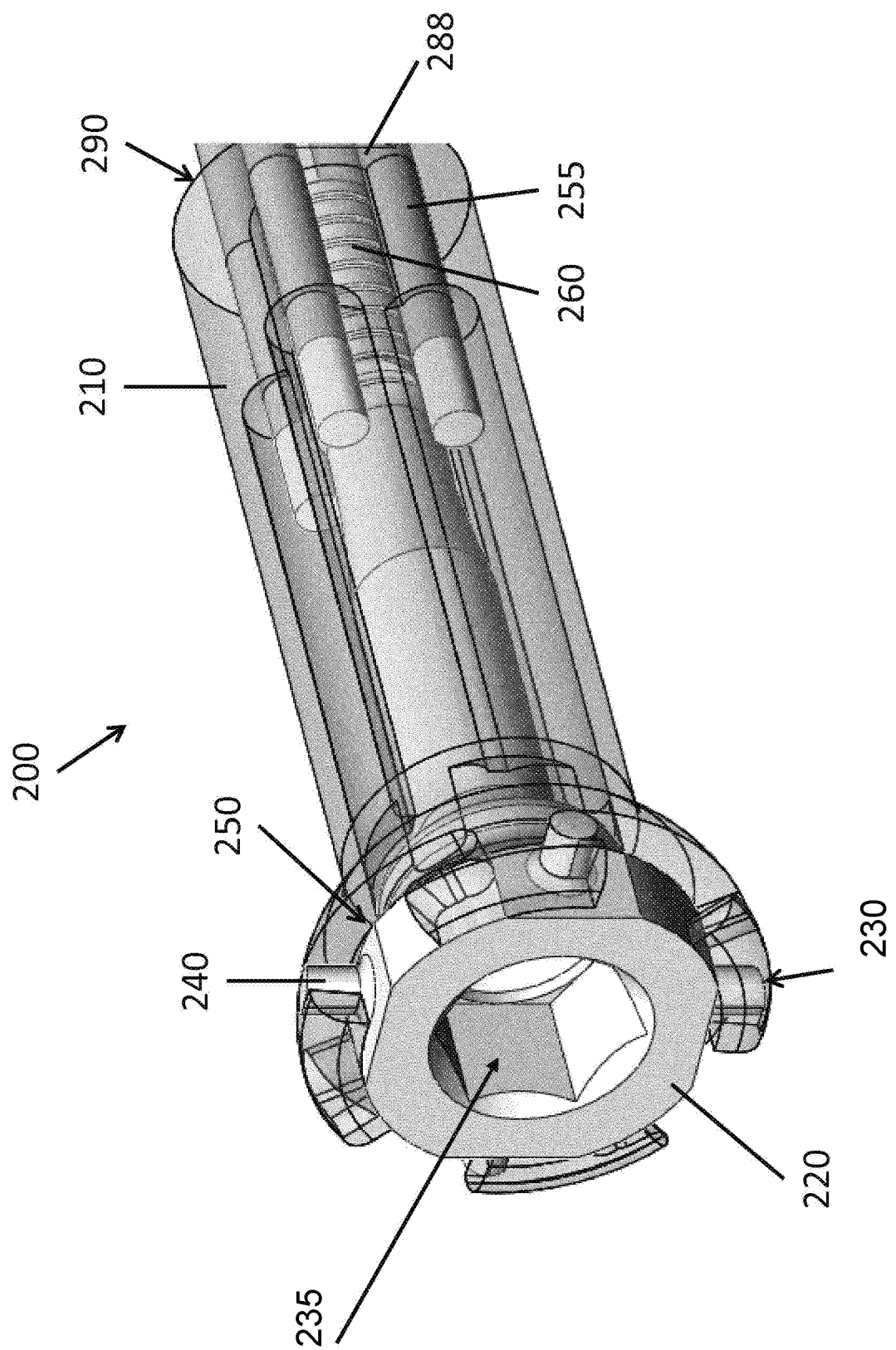

FIGS. 2A and 2B depict an isometric view of a shape locking section 200 of an intramedullary fixation device in an unlocked state in accordance with an illustrative embodiment. Shape locking section 200 includes an outer housing 210 and an inner compression member 220 positioned within outer housing 210. For convenience, FIG. 2B depicts a view of the components of shape locking section 200 within outer housing 210 by making outer housing 210 essentially transparent for purposes of illustration. A plurality of fibers 255 extend into shape locking section 200 through openings 288 in a distal end 290. Inner compression member 220 includes a cam ramp section 260 at a distal end thereof (see FIG. 2B). A portion of fibers 255 within shape locking section 200 is positioned between outer housing 210 and cam ramp section 260 of inner compression member 220 such that rotation of inner compression member 220 may selectively compress the portion of fibers 255 between an inner surface of outer housing 210 and cam ramp section 260 of inner compression member 220, thereby locking fibers 255 in place relative to one another and locking the intramedullary fixation device in a rigid state. In FIGS. 2A and 2B, shape locking section 200 is shown in an unlocked state such that fibers 255 are not compressed between inner compression member 220 and outer housing 210.

Shape locking section 200 further includes a proximal end 230. A portion of inner compression member 220 at proximal end 230 includes a key receiving portion 235. Key receiving portion 235 is configured to receive a key such that the key may be used to selectively rotate inner compression member 220 relative to outer housing 210. In an embodiment, key receiving portion 235 includes a negative relief having a hexagonal perimeter shape such that key receiving portion 235 may receive a hexagonal-shaped key. In alternative embodiments, key receiving portion 235 have any desired perimeter shape suitable for receiving an appropriately shaped key for rotating inner compression member 220 relative to outer housing 210. For example, key receiving portion 235 may have a triangular, rectangular, octagonal, or any other suitable shape.

Inner compression member 220 further includes a plurality of posts 240 that extend from an outer surface. Posts 240 are positioned within respective corresponding slots 250 of outer housing 210. FIGS. 2A and 2B depict four posts 240 and four slots 250, however alternative configurations may include more or fewer post and slot combinations. The configuration of posts 240 and slots 250 limits the maximum possible rotation angle of inner compression member 220 relative to outer housing 210. In an embodiment, slot 250 is sized to enable a sixty degree rotation of inner compression member 220 relative to outer housing 210. In alternative embodiments, other suitable rotation angles are possible. In the unlocked state of shape locking section 200 depicted in FIGS. 2A and 2B, posts 240 are positioned at respective first ends of corresponding slots 250. Upon transitioning to the locked state which involves a sixty degree rotation of inner compression member 220 within outer housing 210, posts 240 are removed to respective second ends of corresponding slots 250 which are opposite the first ends of slots 250 (see, e.g., FIGS. 8A and 8B).

Outer housing 210 further includes a plurality of tool receiving gaps 245 at proximal end 230. FIGS. 2A and 2B depict four tool receiving gaps 245, however alternative configurations may include more or fewer tool receiving gaps. Tool receiving gaps 245 are configured to receive a tool for advancing the intramedullary fixation device within an intramedullary space of a bone. In an embodiment, each of tool receiving gaps 245 receives a tooth of a device advancement tool which may be used to apply both a blunt force as well as a rotary force on the intramedullary fixation device. As such, the device advancement tool may assist in advancing the intramedullary fixation device through hammering, screwing, or other advancement actions. Tool receiving gaps 245 extend into corresponding respective slots 250. In an embodiment, tool receiving gaps 245 have a width that is small enough such that tool receiving gaps 245 do not overlap positions at the first and second ends of slots 250 in which posts 240 are positioned during the locked and unlocked states of shape locking section 230. In this way, the teeth of a device advancement tool will not contact the posts 240 when the device advance tool is applied to the intramedullary fixation device.

Figure 3A:
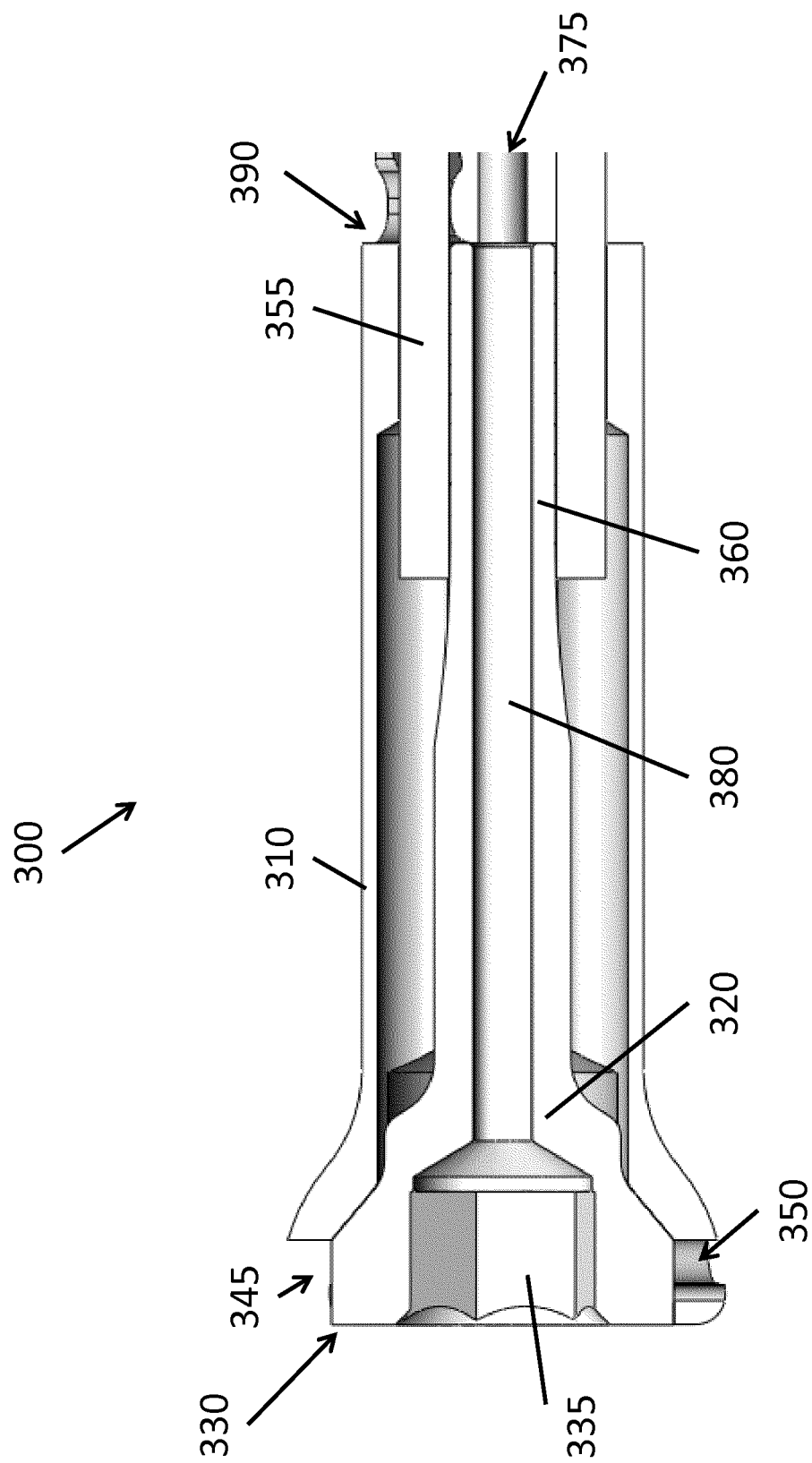
FIGS. 3A and 3B depict cross-sectional views of a shape locking section of an intramedullary fixation device in an unlocked state in accordance with an illustrative embodiment.
Figure 3B:
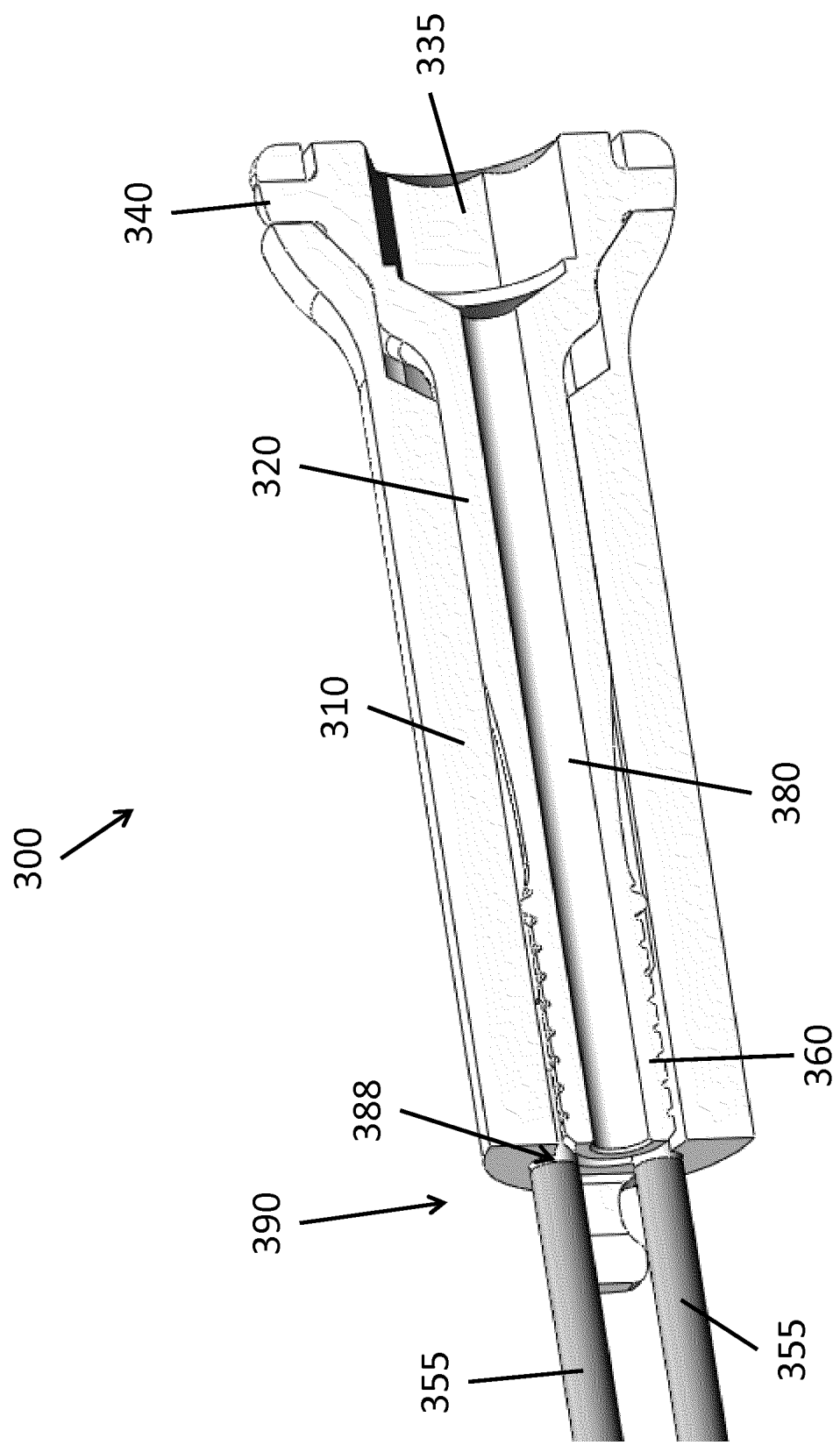
Figure 3C:
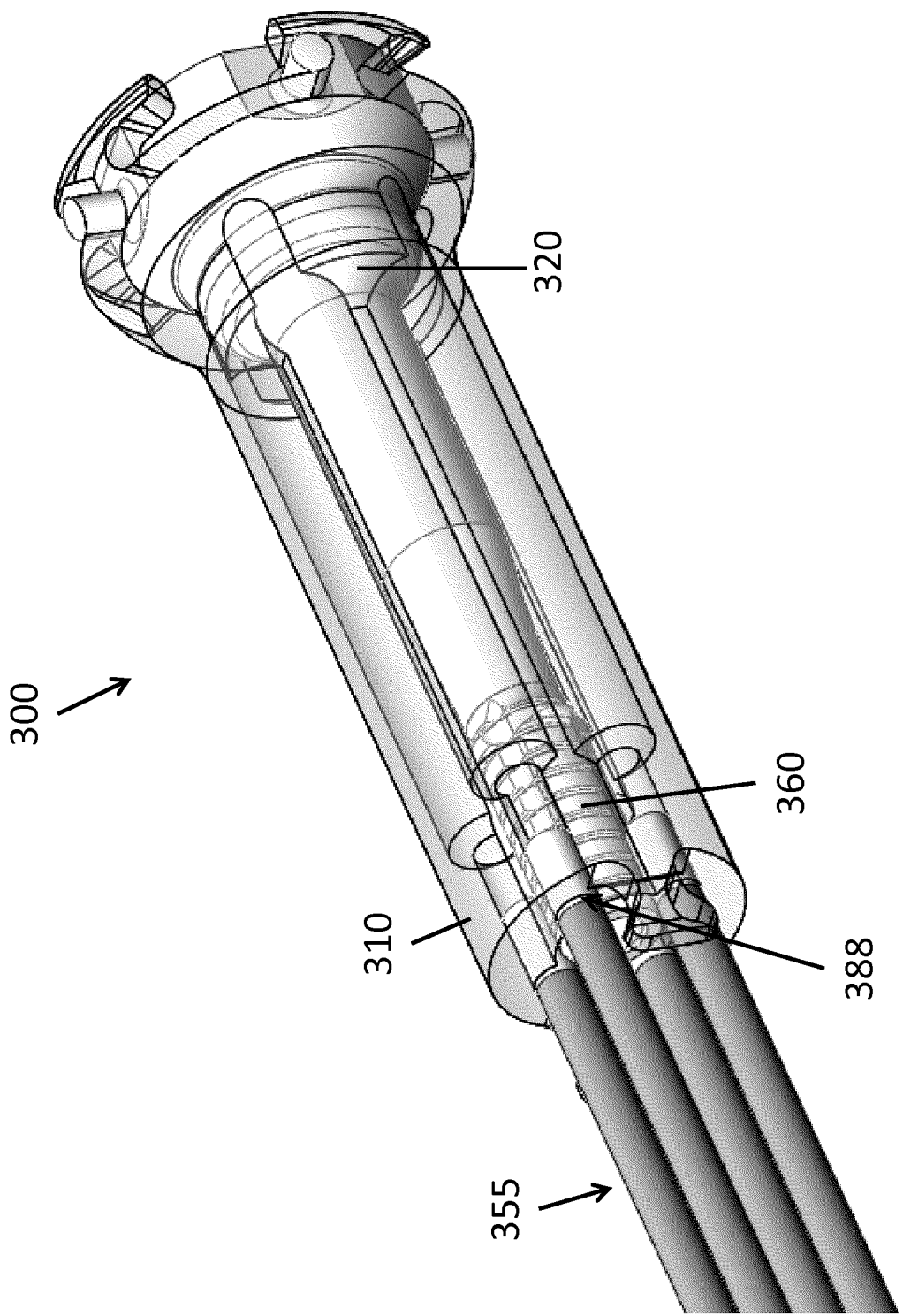
FIG. 3C depicts an isometric view of a shape locking section and fibers of an intramedullary fixation device shown with a transparent housing layer in accordance with an illustrative embodiment.

FIGS. 3A and 3B depict cross-sectional views of a shape locking section 300 of an intramedullary fixation device in an unlocked state in accordance with an illustrative embodiment. FIG. 3C depicts an isometric view of shape locking section 300 and fibers 355 of an intramedullary fixation device shown with a transparent housing layer (310) in accordance with an illustrative embodiment. In an embodiment, shape locking section 300 is the same as shape locking section 200 discussed herein. Similar to shape locking section 200, shape locking section 300 includes an inner compression member 320 located within an outer housing 310. A plurality of fibers 355 extend through openings 388 at a distal end of shape locking section 300 and are located between an inner surface of outer housing 310 and a cam ramp section 360 of inner compression member 320. In an embodiment, openings 388 include partial columns formed within an inner surface of outer housing 310 that extend along a partial length of the interior of shape locking section 310. These columns may be considered partial in that at least a portion of the column is open such that fibers extending within the column are exposed to a surface of cam ramp section 360 to facilitate selective compression between cam ramp section 360 and an inner surface of outer housing 310. Outer housing 310 further includes a plurality of tool receiving gaps 345, a plurality of post-receiving slots 350, and a key receiving portion 335 at a proximal end 330 of shape locking section 300.

Shape locking section 300 further includes a central bore 380 extending through inner compression member 320 along a central axis. Shape locking section 200 includes a similar central bore (not shown in FIGS. 2A and 2B). Central bore 380 extends from a distal end of key receiving portion 335 through inner compression member 320 to a distal end 390 of shape locking section 300. Central bore 380 is configured to receive (or extend over) a guide wire inserted into the intramedullary space of a bone to be fixated. In an embodiment, shape locking section 300 (as well as other portions of an intramedullary fixation device) may be slid over a guidewire such that the guidewire extends through central bore 380. For illustrative purposes, FIG. 3A depicts an example guidewire 375 extending into central bore 380 from distal end 390. It should be recognized that guidewire 375 is a separate component from shape locking section 300 that may be used in conjunction with shape locking section 300 to perform bone fixation operations on a patient.

Figure 4F:
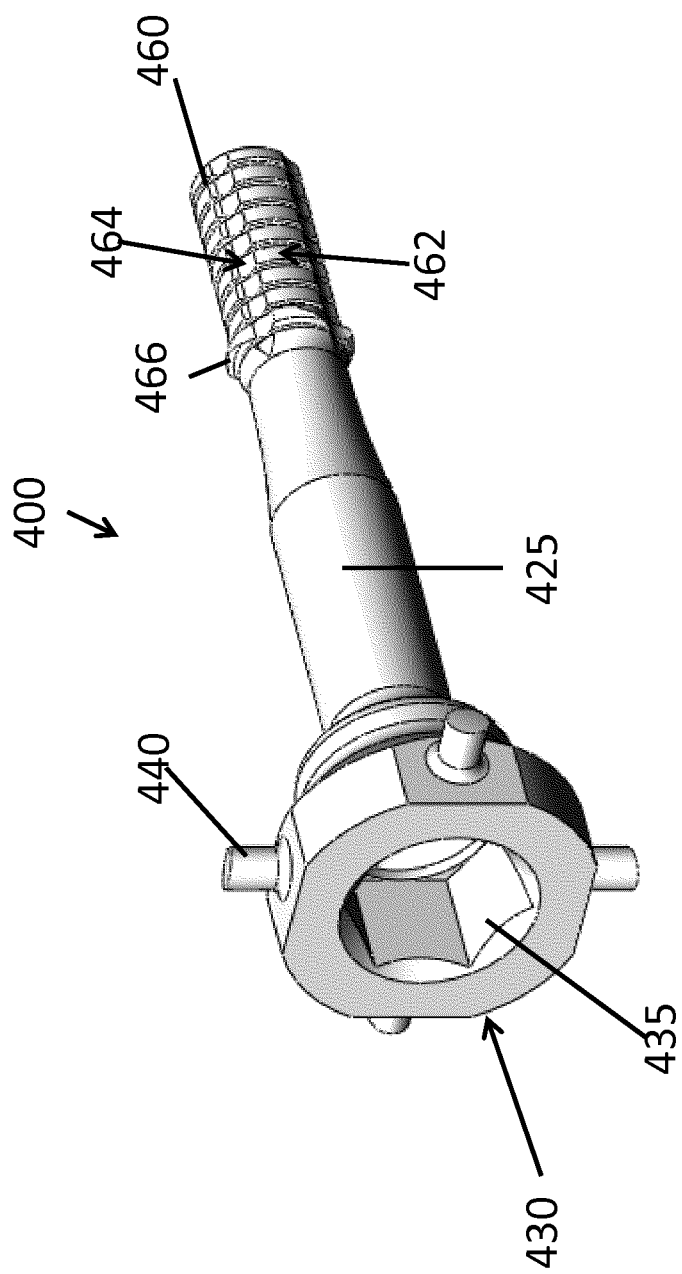

FIGS. 4A-4F depict various views of an inner compression member 400 of a shape locking section in accordance with an illustrative embodiment. FIG. 4A depicts an end view of inner compression member 400, and FIG. 4B depicts a side view of inner compression member 400. FIG. 4C depicts a cross sectional view of inner compression member 400 along line A-A from FIG. 4B. FIG. 4D depicts a cross sectional view of inner compression member 400 along line B-B from FIG. 4A. FIG. 4E depicts a cross sectional view of inner compression member 400 along line C-C from FIG. 4B. FIG. 4F depicts an isometric view of inner compression member 400 in accordance with an illustrative embodiment.

Inner compression member 400 includes a key receiving portion 435 and posts 440 at a proximal end 430. Key receiving portion 435 is configured to receive a key such that the key may be used to selectively rotate inner compression member 420 relative to an outer housing. Key receiving portion 435 includes a negative relief having a perimeter shape that corresponds to a suitable rotation key. A hollow core 480 extends from a distal end of key receiving portion 435 through a central body portion 425 and a cam ramp portion 460 of inner compression member 400.

Cam ramp portion 460 includes a plurality of outermost compression surfaces 462 and a plurality of concave portions 464. In the embodiment of FIGS. 4A-4F, cam ramp portion includes four outermost compression surfaces 462 and four concave portions 464, although different quantities are possible in other implementations. Concave portions 464 include recesses formed in the surface of cam ramp section 460 which extend longitudinally along an axis parallel to a central axis of inner compression member 420. As depicted in FIG. 4C, an outermost portion of compression surfaces 462 extends a greater radial distance from a center of cam ramp section 460 than an outermost portion of concave portions 464. As such, when inner compression member 400 is turned such that compression surfaces 462 are adjacent to fibers extending into inner compression member 400, compression surfaces 462 push the fibers outward, compressing the fibers against an inner surface of an outer housing within which inner compression member 400 is positioned.

In contrast, when the intramedullary fixation device is in an unlocked (or flexible) state, inner compression member 400 is turned such that concave portions 464 are adjacent to the fibers. As such, at least a portion of the fibers would sit within (or along) concave portions 464. Because concave portions 464 do not extend radially outward as far as compression surfaces 462, the fibers would not be compressed against the inner surface of the outer housing. Indeed, concave portions 464 are recessed a sufficient distance to allow substantially free movement of the fibers between inner compression member 400 and the outer housing of the shape locking section.

Cam ramp section 460 further includes a plurality of proximal ridge members 466 at a proximal end. Proximal ridge members 466 extend a greater radial distance from a center of cam ramp section 460 than the outermost portions of compression surfaces 462. In addition, like with compression surfaces 462, concave portions 464 extend between adjacent pairs of proximal ridge members 466. As shown in FIG. 4E, the combination of adjacent respective proximal ridge members 466 and concave portions 464 create a cam configuration that facilitates rotation and locking of inner compression member 400 relative to the outer housing within the shape locking section.

Figure 5B:
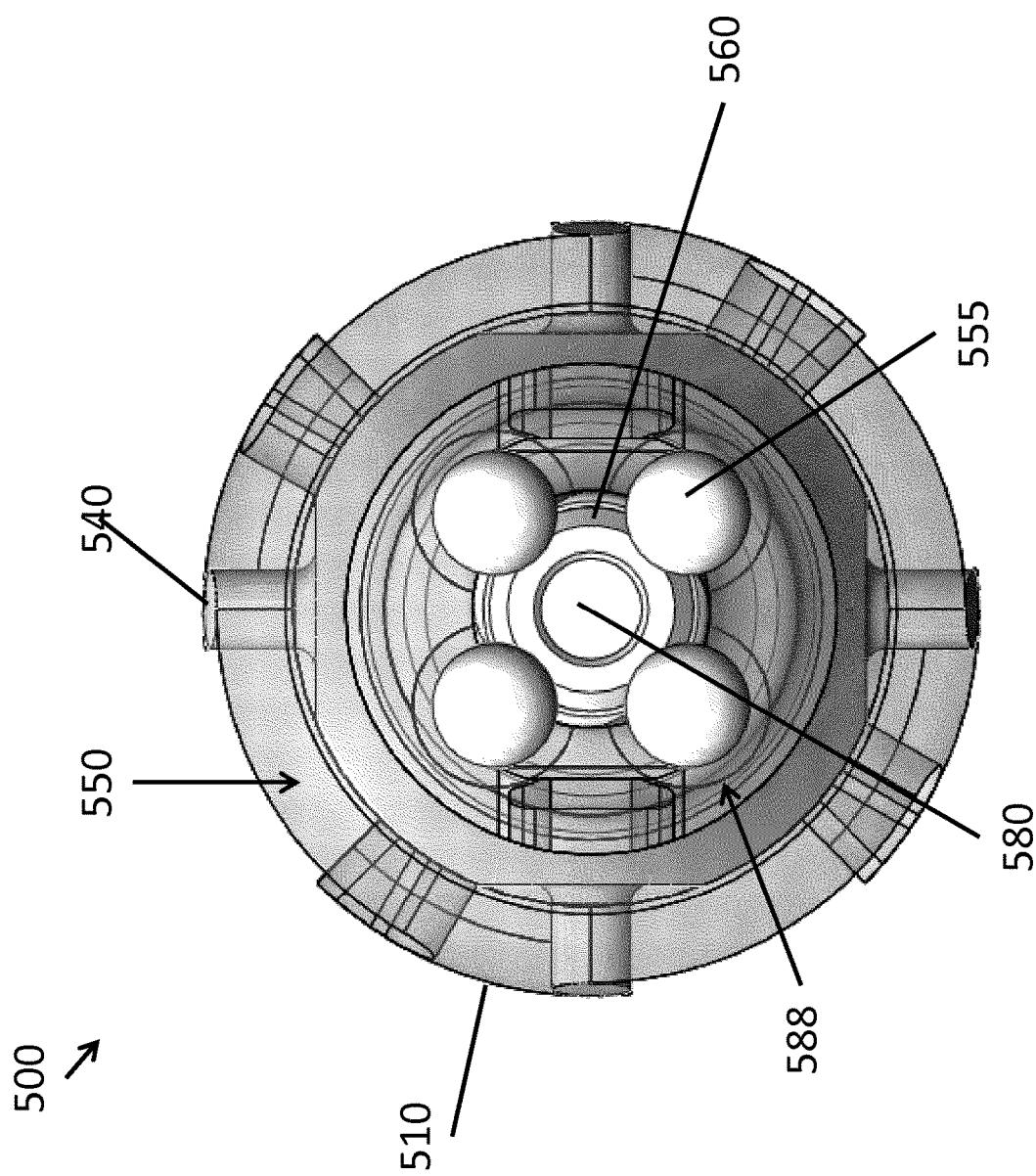

FIGS. 5A and 5B depict an end view of a distal end of a shape locking section 500 in an unlocked state in accordance with an illustrative embodiment. In an embodiment, shape locking section 500 is the same as shape locking sections 200 and 300 discussed herein. Shape locking section 500 includes an inner compression member located within an outer housing 510. A plurality of fibers 555 extend through openings 588 at the distal end of shape locking section 500 and are located between an inner surface of outer housing 510 and a cam ramp section 560 of inner compression member. Outer housing 510 further includes a plurality of tool receiving gaps 545 and a plurality of post-receiving slots 550 having a corresponding plurality of posts 540 therein. Shape locking section 500 further includes a central bore 580 extending through inner compression member along a central axis. Shape locking section 500 also includes a tab 565 that is configured to mate with a corresponding slot in a proximal most segment of a main body portion of the intramedullary fixation device. Tab 565 thus facilitates a mechanical connection between shape locking section 500 and a proximal end of a main body portion of the intramedullary fixation device. In an embodiment, the proximal end of the main body portion may be a proximal-most individual segment of the main body portion.

Figure 6A:
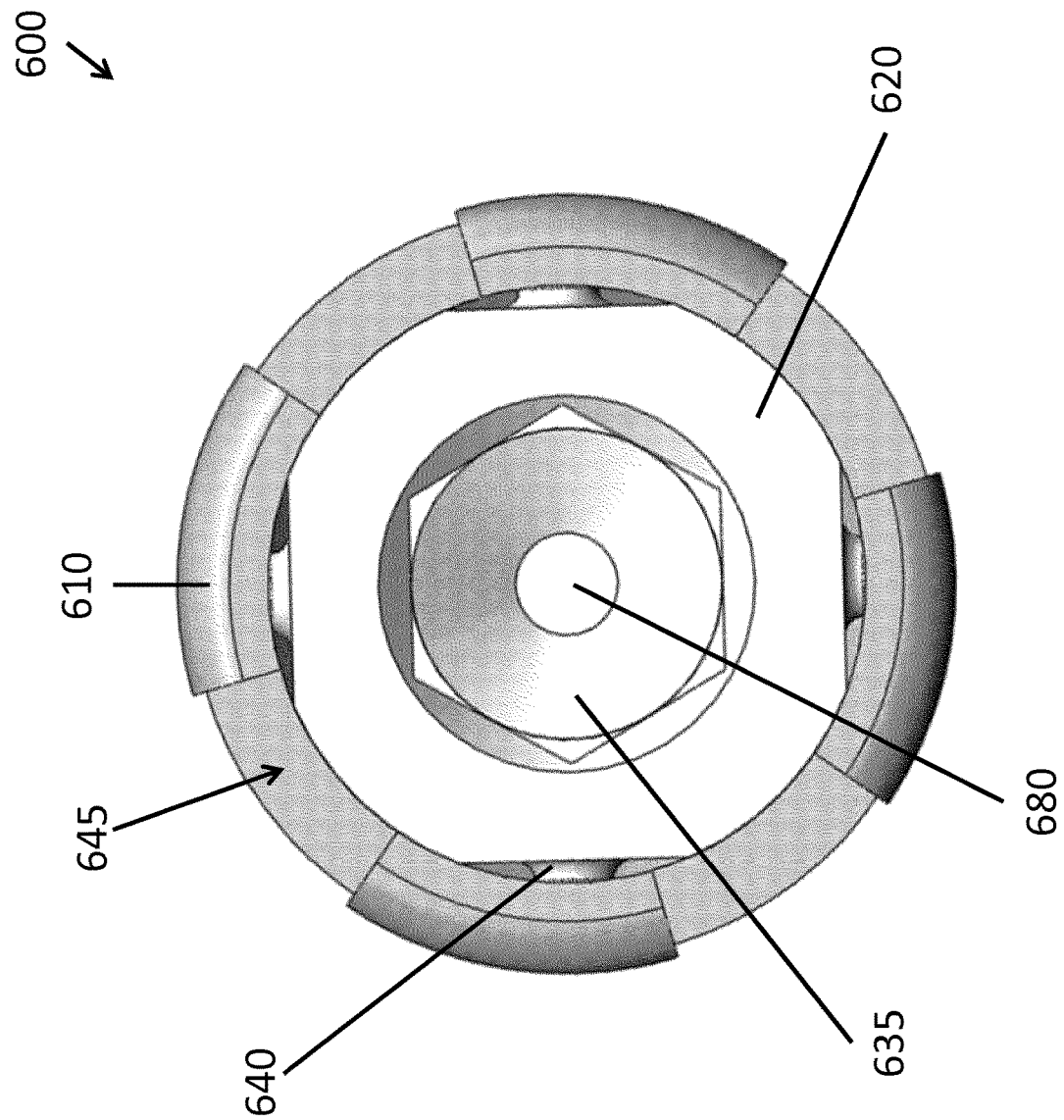
FIGS. 6A and 6B depict end views of a proximal end of a shape locking section in an unlocked state in accordance with an illustrative embodiment.
Figure 6B:
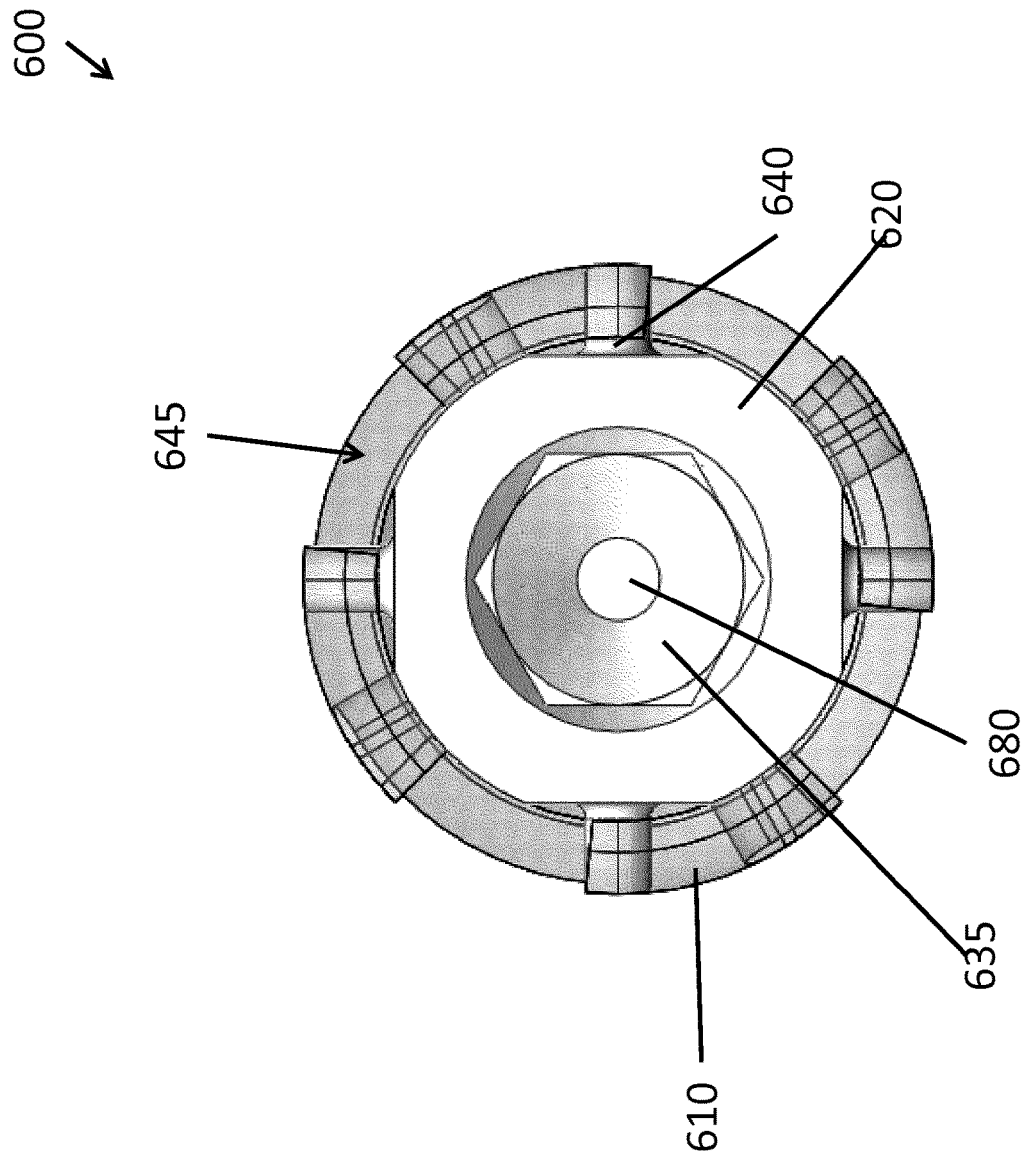

FIGS. 6A and 6B depict an end view of a proximal end of a shape locking section 600 in an unlocked state in accordance with an illustrative embodiment. In an embodiment, shape locking section 600 is the same as shape locking sections 200, 300, and 500 discussed herein. Shape locking section 600 includes an inner compression member 620 located within an outer housing 610. Outer housing 610 includes a plurality of tool receiving gaps 645 and a plurality of post-receiving slots having a corresponding plurality of posts 640 therein. A portion of inner compression member 620 includes a key receiving portion 635. Key receiving portion 635 is configured to receive a key such that the key may be used to selectively rotate inner compression member 620 relative to outer housing 610. In an embodiment, key receiving portion 635 includes a negative relief having a hexagonal perimeter shape such that key receiving portion 635 may receive a hexagonal-shaped key. In alternative embodiments, key receiving portion 635 have any desired perimeter shape suitable for receiving an appropriately shaped key for rotating inner compression member 620 relative to outer housing 610. Shape locking section 600 further includes a central bore 680 extending from a distal end of key receiving portion 635 through and along a central axis of inner compression member 620.

Figure 7A:
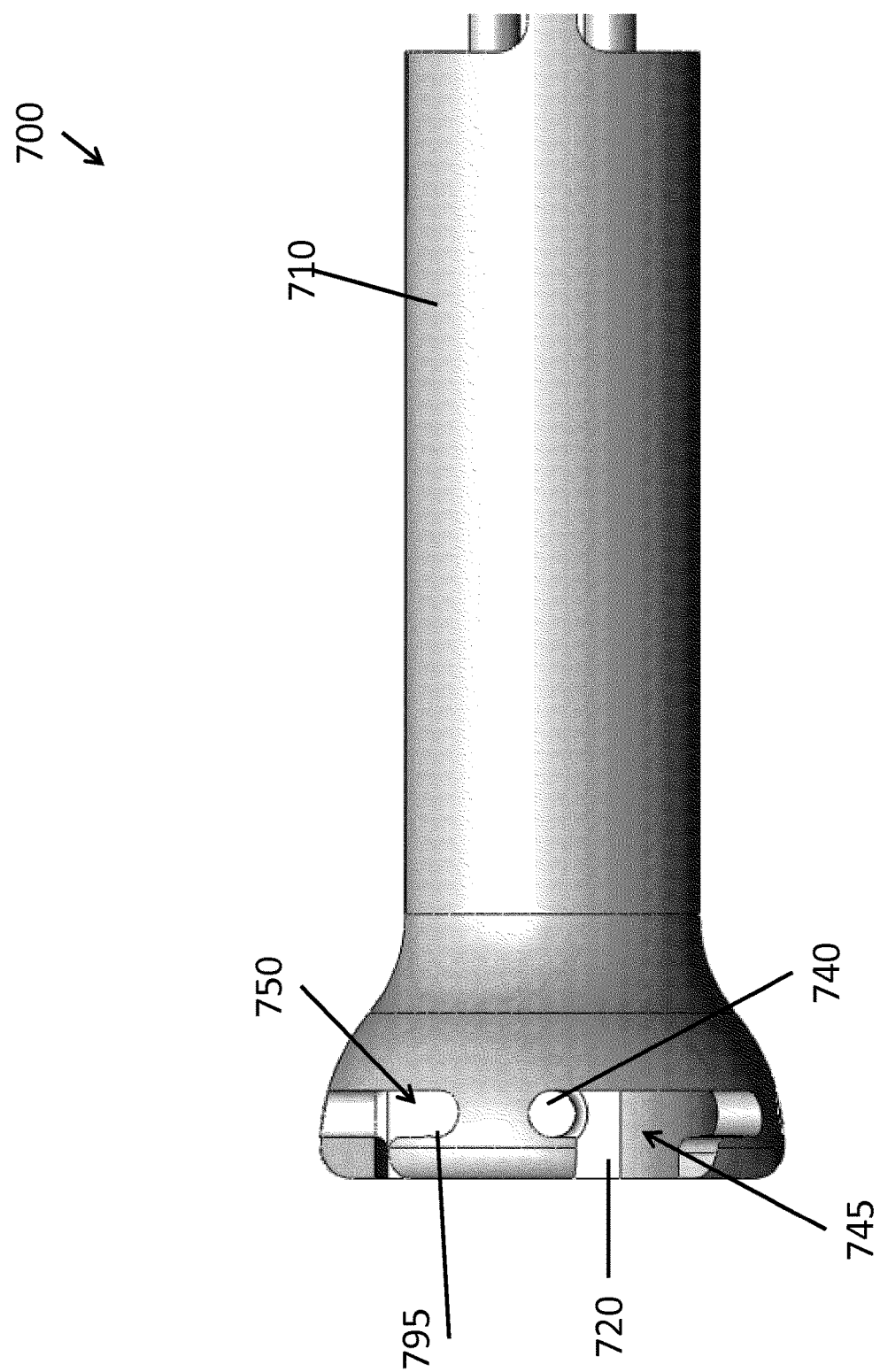
FIG. 7A depicts a side elevation view of a shape locking section of an intramedullary fixation device in an unlocked state in accordance with an illustrative embodiment.
Figure 7B:
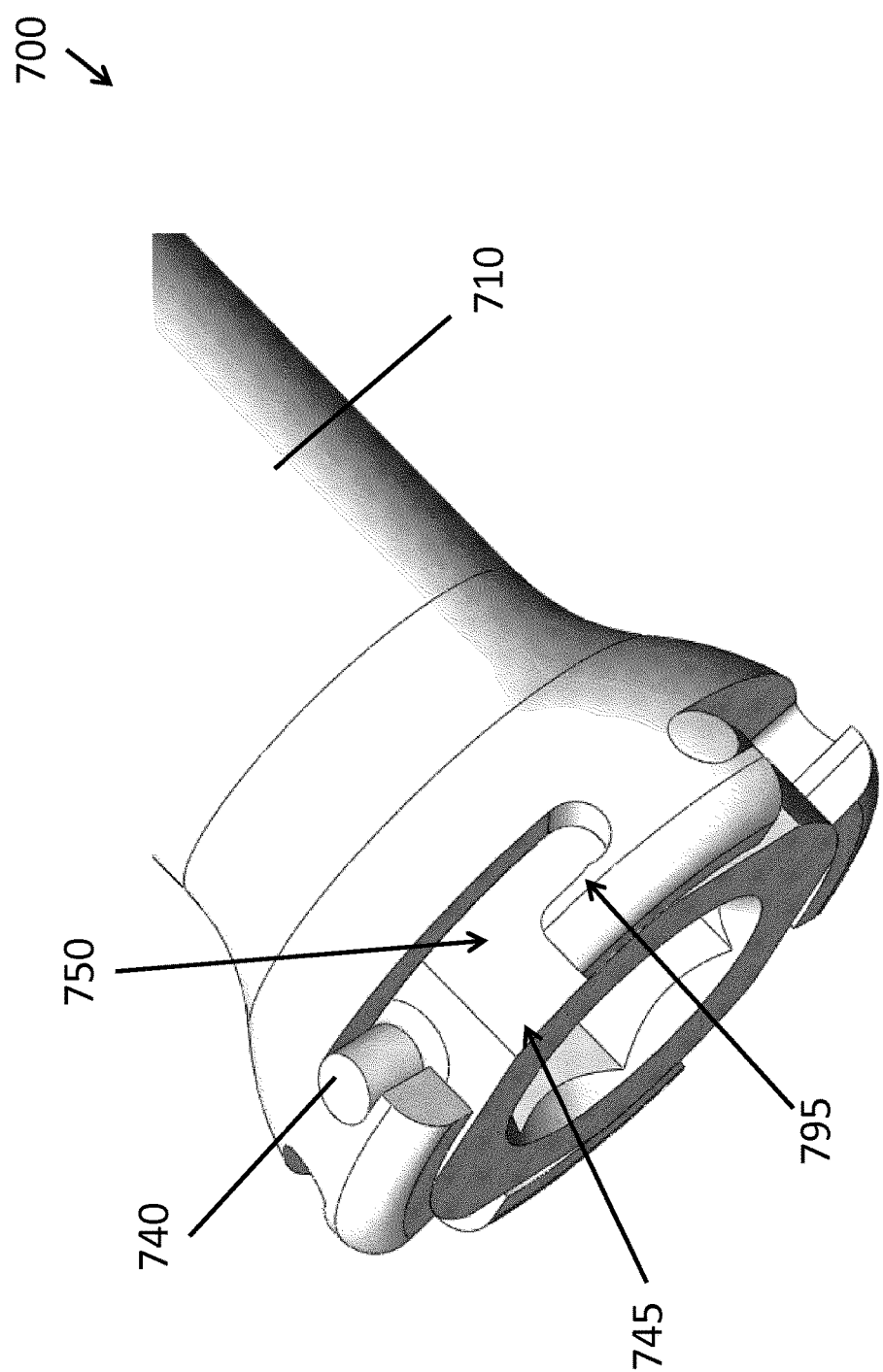
FIG. 7B depicts an isometric view of a proximal end of a shape locking section in accordance with an illustrative embodiment.

FIG. 7A depicts a side elevation view of a shape locking section 700 of an intramedullary fixation device in an unlocked state in accordance with an illustrative embodiment. FIG. 7B depicts an isometric view of a proximal end of shape locking section 700 in accordance with an illustrative embodiment. In an embodiment, shape locking section 700 is the same as shape locking sections 200, 300, 500, and 600 discussed herein. Shape locking section 700 includes an inner compression member 720 located within an outer housing 710. A plurality of fibers extend through a distal end of shape locking section 700 and are located between an inner surface of outer housing 710 and an outer surface of inner compression member 720. Outer housing 710 further includes a plurality of tool receiving gaps 745 and a plurality of post-receiving slots 750 at a proximal end of shape locking section 700. A plurality of corresponding posts 740 are positioned within each respective post-receiving slot 750. Posts 740 extend from an outer surface of inner compression member 720.

In an embodiment, slots 750 include a post retention tab 795. Post retention tab 795 includes a bump or irregularity along a surface of slot 750 that extends into an interior of slot 750. In an embodiment, slot 750 assists in maintaining post 740 in a desired position within the slot. For example, when transitioning shape locking section 700 from an unlocked state to a locked state, post 740 may be rotated from a position at a first end of slot 750 to a position at an opposite second end of slot 750. Post retention tab 795 may be positioned a sufficient distance from the second end of slot 750 to help maintain post 740 at the position at the second end of slot 750. In an embodiment, this distance may be equal to or slightly larger than a diameter of post 740. Post retention tab 795 may also provide an audible signal that the post 740 has been placed into the locked position at the second end of slot 750. For example, as post 740 is passed over post retention tab 795, a clicking sound may be emitted due to interference of post retention tab 795 with post 740. Furthermore, a surgeon may feel post 740 encountering and sliding past post retention tab 795, thus providing an additional feel indicator that shape locking section 700 has been successfully transitioned to a locked state. In alternative embodiments, a corresponding post retention tab may also be positioned with respect to the first end of slot 750 associated with the unlocked state of shape locking section 700. Such a tab may help maintain the shape locking section 700 in an unlocked state and assist in indicating to a surgeon when post 740 is removed from the position at the first end of slot 750 (and thus shape locking section 700 transitioned from the unlocked, flexible state).

Figure 8A:
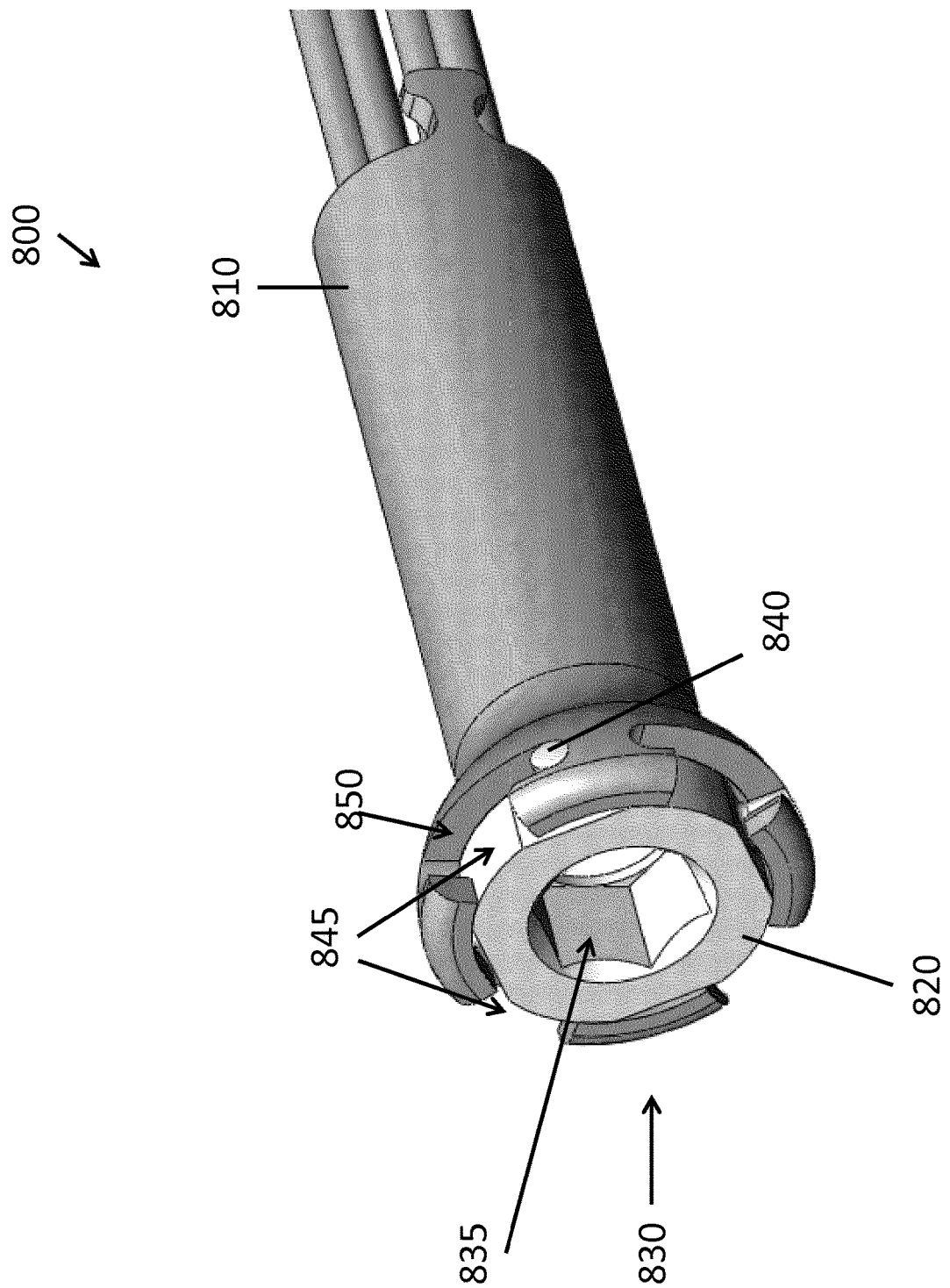
FIGS. 8A and 8B depict isometric views of a shape locking section of an intramedullary fixation device in a locked state in accordance with an illustrative embodiment.
Figure 8B:
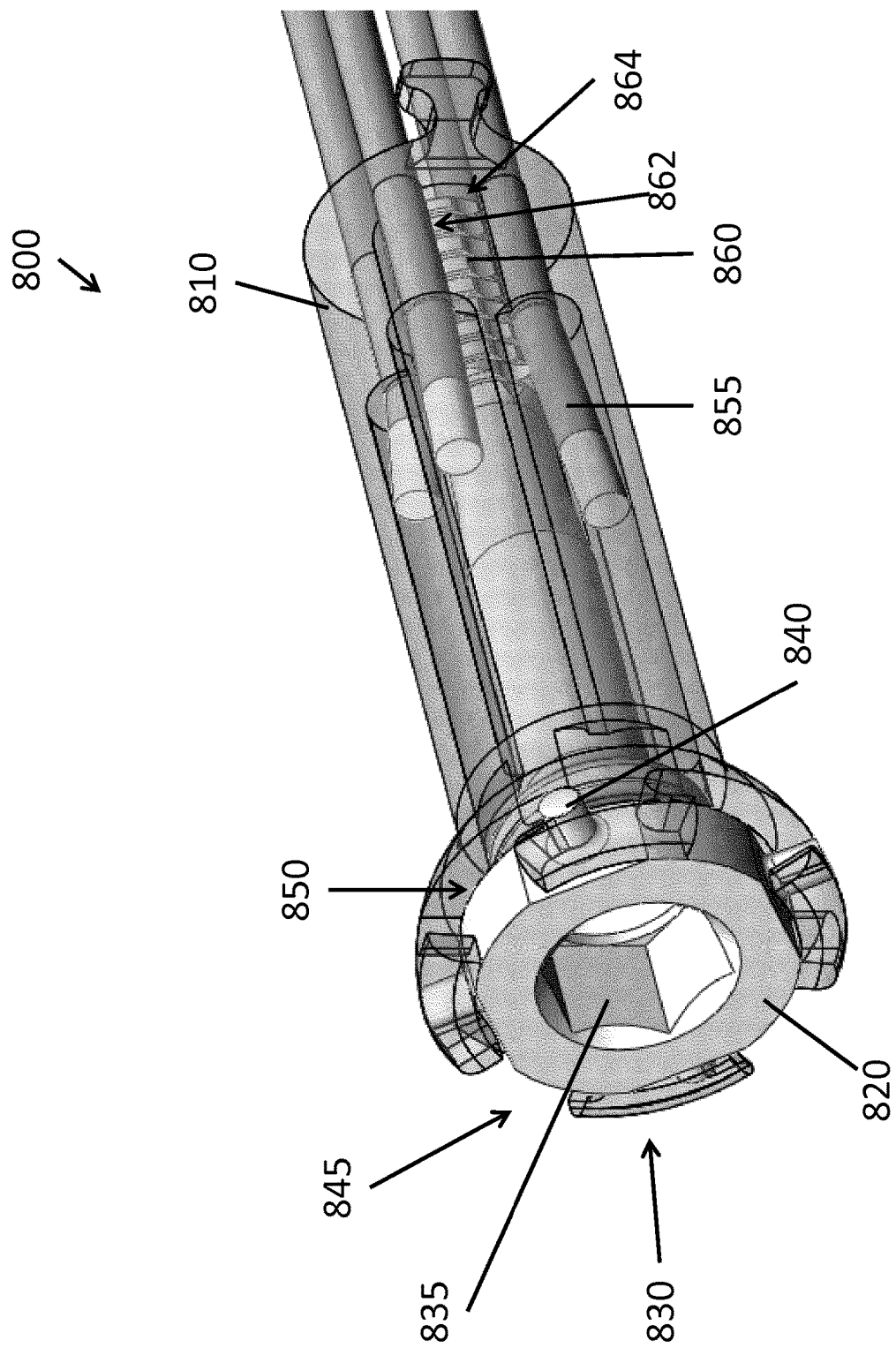

FIGS. 8A and 8B depict an isometric view of a shape locking section 800 of an intramedullary fixation device in a locked state in accordance with an illustrative embodiment. In an embodiment, shape locking section 800 is the same as the various shape locking sections discussed herein. As with the other shape locking sections discussed herein, shape locking section 800 includes an outer housing 810 and an inner compression member 820 positioned within outer housing 810. For convenience, FIG. 8B depicts a view of the components of shape locking section 800 within outer housing 810 by making outer housing 810 essentially transparent.

A plurality of fibers 855 extend through a distal end of shape locking section 800 and are located between an inner surface of outer housing 810 and a cam ramp section 860 of inner compression member 820 (see FIG. 8B). Outer housing 810 further includes a plurality of tool receiving gaps 845, a plurality of post-receiving slots 850, and a key receiving portion 835 at a distal end 830 of shape locking section 800.

In FIGS. 8A and 8B, shape locking section 800 is shown in a locked state such that fibers 855 are compressed between an inner surface of outer housing 810 and cam ramp section 860 of inner compression member 820. FIG. 8B depicts cam ramp section 860 in a rotated position from that depicted in FIG. 2B (which depicts shape locking section 200 in an unlocked state). Cam ramp section 860 includes a compression surface 862 and a concave portion 864. Concave portion 864 is a recess formed in the surface of cam ramp section 860 which extends longitudinally along an axis parallel to the central axis of inner compression member 820. As depicted in FIG. 8B, an outermost portion of compression surface 862 extends a greater radial distance from a center of cam ramp section 860 than an outermost portion of concave portion 864. As such, when inner compression member 820 is turned such that compression surface 862 is adjacent to fibers 855, compression surface 862 pushes fibers 855 outward and compresses fibers 855 against an inner surface of outer housing 810.

In contrast, when shape locking section 800 is in an unlocked (or flexible) state, inner compression member 820 is turned such that concave portion 864 adjacent to fibers 855. As such, fibers 855 would sit within concave portion 864. Such positioning is shown, for example, in FIG. 2B. Because concave portion 864 does not extend radially outward as far as compression surface 862, fibers 855 are not compressed against the inner surface of outer housing 810. Indeed, concave portion 864 is recessed a sufficient distance (relative to the inner surface of outer housing 810 and compression surface 862) to allow substantially free movement of fibers 855 within shape locking section 800.

Inner compression member 820 further includes a key receiving portion 835 at proximal end 830. Key receiving portion 835 is configured to receive a key that may be used to selectively rotate inner compression member 820 relative to outer housing 810 between a locked position and an unlocked position. Inner compression member 820 further includes a plurality of posts 840 that are positioned within respective corresponding slots 850 of outer housing 810. In the locked state of shape locking section 800 depicted in FIGS. 8A and 8B, posts 840 are positioned at respective second ends of corresponding slots 850. In contrast, as discussed above, FIGS. 2A and 2B depict an unlocked state of shape locking section 200 in which posts 240 are positioned at respective first ends of corresponding slots 250. Upon transition between the locked and unlocked states, inner compression member 220/820 is rotated within outer housing 210/810, such that posts 240/840 are moved between the first and second ends of corresponding slots 250/850.

Outer housing 810 further includes a plurality of tool receiving gaps 845 at proximal end 830. As discussed generally herein, tool receiving gaps 845 are configured to receive a tool for advancing the intramedullary fixation device within an intramedullary space of a bone.

Figure 9:
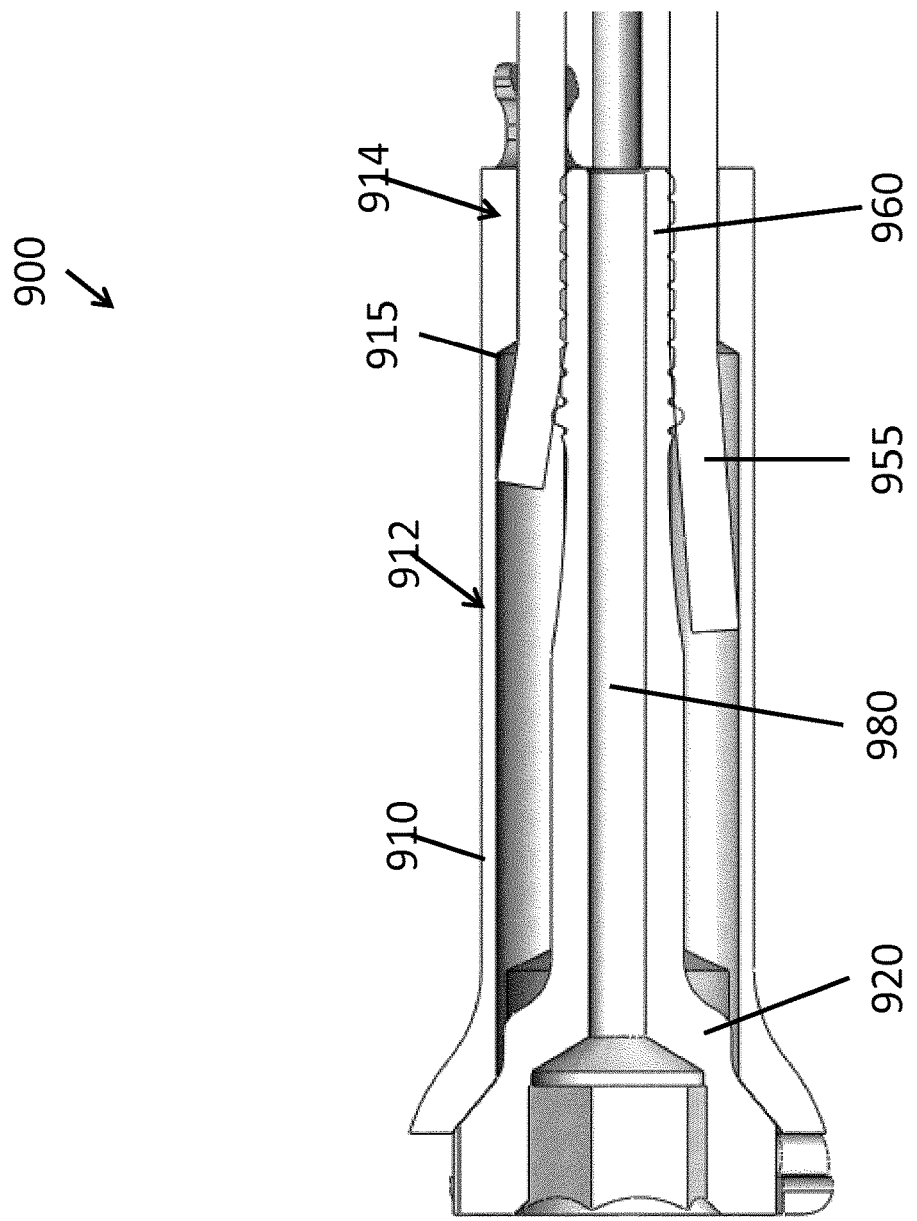
FIG. 9 depicts a cross-sectional view of a shape locking section of an intramedullary fixation device in a locked state in accordance with an illustrative embodiment.

FIG. 9 depicts a cross-sectional view of a shape locking section 900 of an intramedullary fixation device in a locked state in accordance with an illustrative embodiment. In an embodiment, shape locking section 900 is the same as the other various shape locking sections discussed herein. Similar to the other shape locking sections, shape locking section 900 includes an inner compression member 920 located within an outer housing 910. A central bore 980 extends through inner compression member 320 along a central axis. A plurality of fibers 955 extend through a distal end of shape locking section 900 and are located between an inner surface of outer housing 910 and a cam ramp section 960 of inner compression member 920. Inner compression member 920 and cam ramp section 960 are positioned such that an outermost compression surface of cam ramp section 960 presses fibers 955 outward, thereby compressing fibers 955 against an inner surface of outer housing 910. As discussed above, the outermost compression surface of cam ramp section 960 extends a greater radial distance outward than a concave portion of cam ramp section 960 in which fibers 955 are positioned in an unlocked state of shape locking section 900.

The inner surface of outer housing 910 includes a transition portion 915 that transitions from a first portion 912 of outer housing 910 having an inner surface with a relatively large diameter to a second portion 914 of outer housing 910 having an inner surface with a smaller diameter than that of the first portion. The relatively smaller diameter of second portion 914 is sufficient to compress fibers 955 together with cam ramp section 960 when shape locking section 900 is in a locked state, thereby locking fibers 955 in place. In addition, transition portion 915 has the added benefit of causing a kink in fibers 955 when fibers 955 are compressed between cam ramp section 960 and second portion 914 of outer housing 910. The kinking of fibers 955 provides a further locking force on fibers 955.

Figure 10:
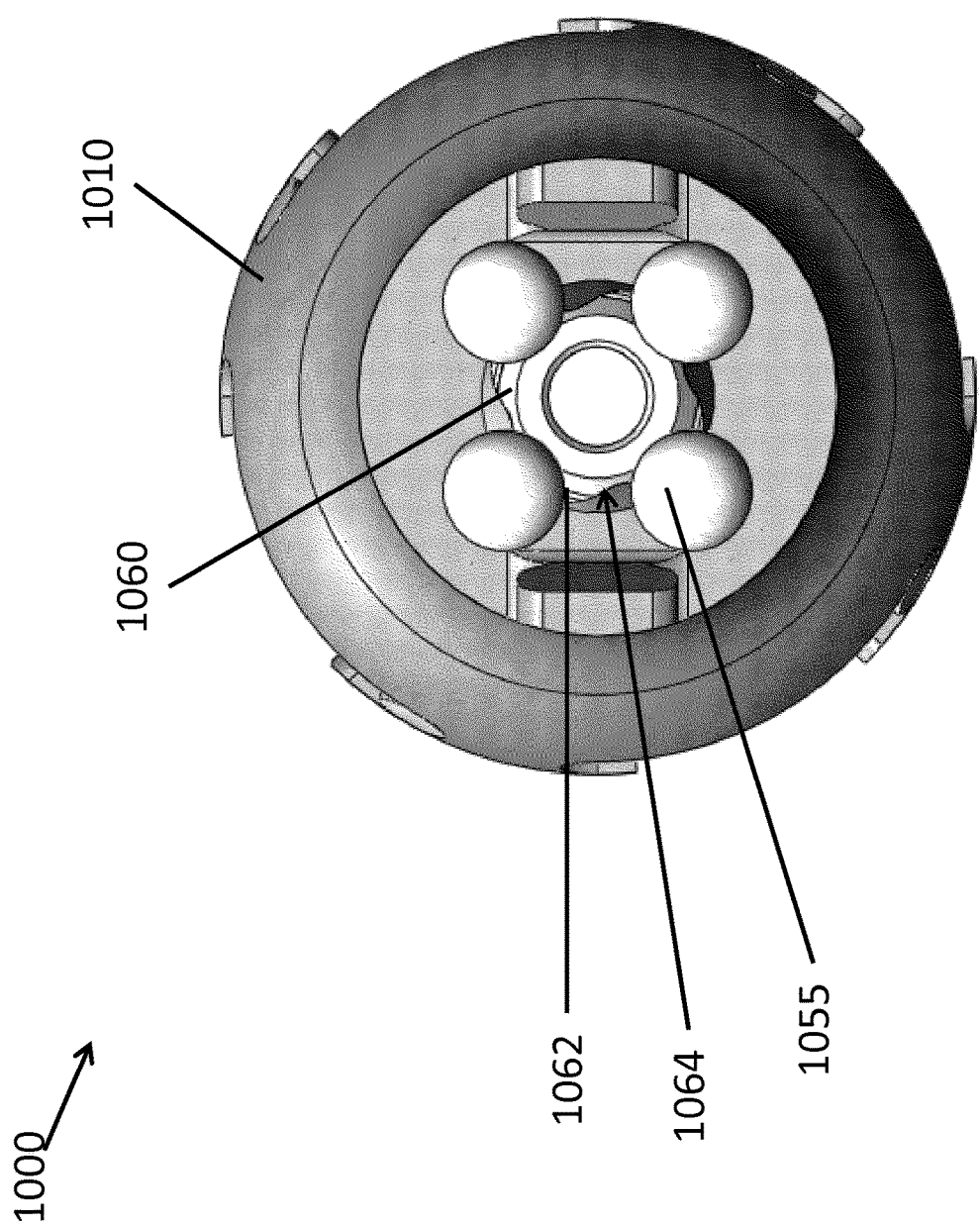
FIG. 10 depicts an end view of a distal end of a shape locking section in a locked state in accordance with an illustrative embodiment.

FIG. 10 depicts an end view of a distal end of a shape locking section 1000 in a locked state in accordance with an illustrative embodiment. Shape locking section 1000 includes an inner compression member located within an outer housing 1010. A plurality of fibers 1055 extend through the distal end of shape locking section 1000 and are located between an inner surface of outer housing 1010 and a cam ramp section 1060 of the inner compression member. As indicated above, shape locking section 1000 is shown in a locked state, i.e., the inner compression member and cam ramp section 1060 are shown rotated relative to outer housing 1010 such that compression surface 1062 is adjacent to and compresses fibers 1055 against an inner surface of outer housing 1010. The rotation of inner compression member and cam ramp section 1060 has moved concave portions 1064 such that fibers 1055 are no longer seated or positioned within concave portions 1064.

Figure 11:
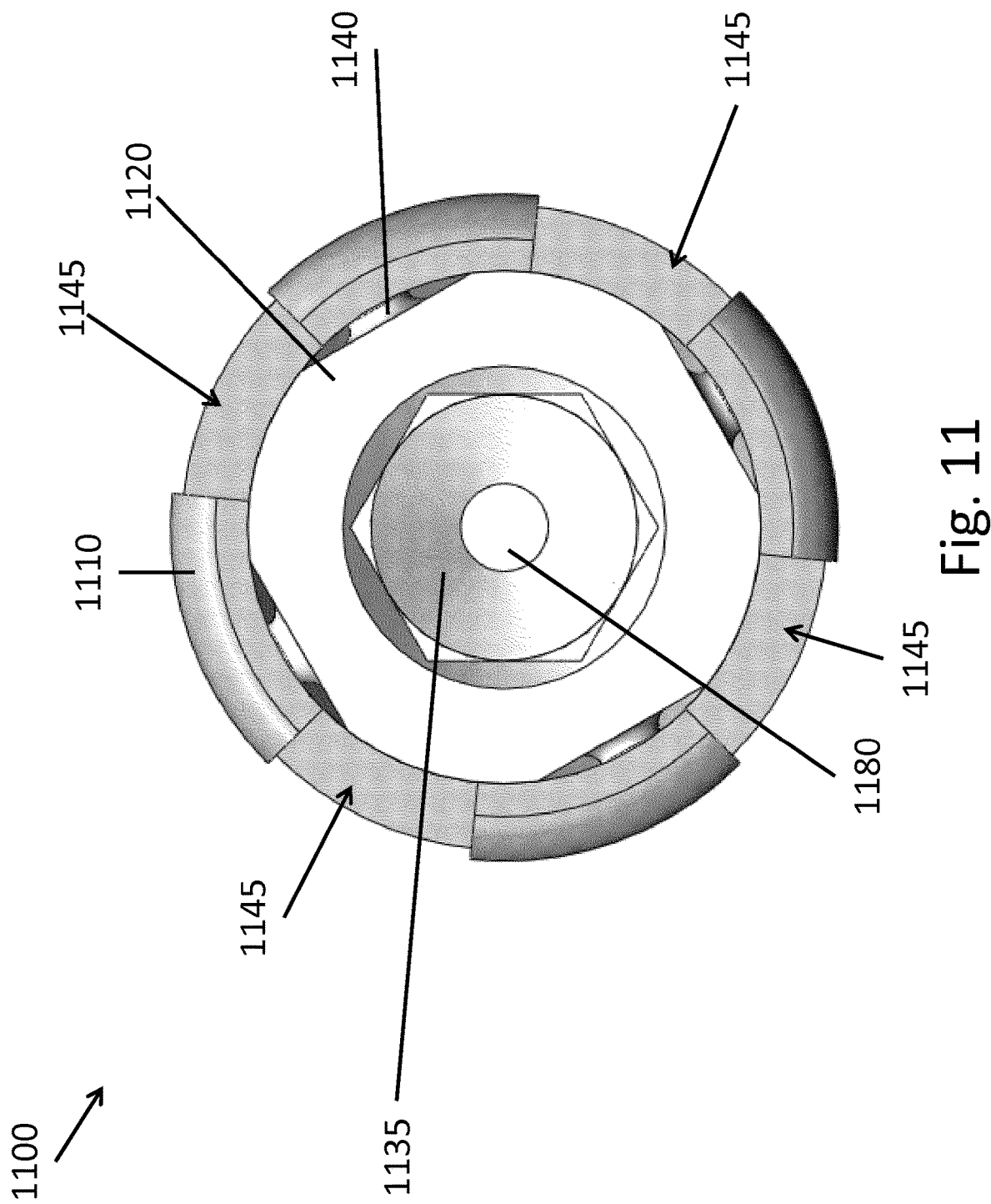
FIG. 11 depicts an end view of a proximal end of a shape locking section in a locked state in accordance with an illustrative embodiment.

FIG. 11 depicts an end view of a proximal end of a shape locking section 1100 in a locked state in accordance with an illustrative embodiment. Similar to shape locking section 600 discussed above with respect to FIGS. 6A and 6B, shape locking section 1100 includes an inner compression member 1120 located within an outer housing 1110. Outer housing 1110 includes a plurality of tool receiving gaps 1145 and a plurality of post-receiving slots having a corresponding plurality of posts 1140 therein. A portion of inner compression member 1120 includes a key receiving portion 1135. Key receiving portion 1135 is configured to receive a key such that the key may be used to selectively rotate inner compression member 1120 relative to outer housing 1110. In an embodiment, key receiving portion 1135 includes a negative relief having a perimeter shape that corresponds to a perimeter shape of a rotation key. Shape locking section 1100 further includes a central bore 1180 extending from a distal end of key receiving portion 1135 through and along a central axis of inner compression member 1120. As indicated above, shape locking section 1110 is configured in a locked state such that inner compression member 1120 has been rotated within outer housing 110 so that posts 1140 are seated within a second end of the corresponding post-receiving slots in the outer housing 110 associated with the locked state.

FIG. 12 depicts a flow diagram for a method 1200 of fixing a reduced bone fragment in accordance with an illustrative embodiment. Method 1200 includes an operation 1210 of creating an entry into a curved bone. In an operation 1220, a guidewire is advanced through a curved intramedullary space to a position distal to a reduced bone fracture. In an operation 1230, a channel in the intramedullary space is reamed along the length of the guidewire suing a reaming tool.

In an operation 1240, an intramedullary fixation device is advanced through the channel in a flexible state and placed into a final position. In the flexible state, the intramedullary fixation device may conform to the curved pathway created by the guidewire and reaming tool. In an embodiment, operation 1240 may include affixing a distal end of the intramedullary fixation device to a bone segment and/or affixing a proximal end of the intramedullary fixation device to another bone segment. The intramedullary fixation device may further include a main body portion and a shape locking section. The main body portion may include a plurality of segments have channels or apertures arranged therein to generally form two or more lumens in the main body when the segments are in mechanical engagement. When in a flexible state, the individual segments may move relative to each other in a first and a second orthogonal plane relative to the main axis. The intramedullary fixation device may have a torque transmission member positioned substantially at the proximal end to facilitate advancement of the device into the intramedullary space. One or more fibers extend through the lumens such that.

In an operation 1250, the intramedullary fixation device is locked in a rigid state. In the rigid state, the intramedullary fixation device may support tensile and vertical shear mechanical loads required to fix the fractured bone segments. In an embodiment, the shape locking section of the intramedullary fixation device is configured to selectively restrain the one or more fibers so as to selectively place the intramedullary fixation device into the rigid (or flexible) state. The shape locking section may be operated by rotating an inner compression member relative to an outer housing. Based on the arrangement of the inner compression member and its cam ramp section relative to the outer housing (as discussed further above), the fibers may be compressed (and thereby restrained) between the inner compression member and the outer housing. Fixation of the fibers provides a fixed, rigid shape to the flexible main body portion of the intramedullary fixation device.

The intramedullary fixation device may be later removed by optionally disengaging the intramedullary fixation segment from the bone segments and returning the device to a flexible state before removing the device from the intramedullary space.

In some examples, a medical apparatus for bone fixation comprises a flexible body defining a main axis, the flexible body having a proximal end and a distal end, wherein the flexible body comprises: a plurality of apertures, the plurality of apertures arranged to generally form a plurality of lumens in the flexible body; a bone engagement feature positioned substantially on the distal end of the flexible body; a plurality of fibers that extend through the lumens; and a shape locking section configured to selectively secure the plurality of fibers such that the flexible body is locked when the fibers are fixed into position relative to each other. In some examples, a compression member may be used to fix the plurality of fibers in place to shape lock the apparatus. In some examples, the plurality of fibers may comprise one or more cables, such as metal cables. In some examples, the shape locking section may comprises an outer housing and an inner compression member configured to rotate within the outer housing. In some examples, the inner compression member may comprise a cam ramp section having a plurality of outer compression surfaces and a plurality of concave portions, wherein each concave portion is positioned between a pair of respective outer compression surfaces. In some examples, at least one of the plurality of fibers is seated within one of the concave portions when the flexible body is in an unlocked state. In some examples, at least one of the plurality of fibers is compressed between one of the outer compression surfaces and an inner surface of the outer housing when the flexible body is in a locked state.

In some examples, a medical apparatus for bone fixation comprises: a flexible body defining a main axis, the flexible body having a proximal end and a distal end, wherein the flexible body comprises: a bone engagement feature positioned substantially on the distal end of the flexible body; and a shape locking section configured to selectively secure a plurality of fibers such that the flexible body is locked when the fibers are fixed into position, and wherein the shape locking section includes at least one compression member configured to fix the fibers in the locked state. In some examples, the shape locking section comprises an outer housing and an inner compression member configured to rotate within the outer housing. In some examples, the shape locking section comprises a torque transmission engagement feature positioned at a proximal end. In some examples, the inner compression member comprises a cam ramp section having a plurality of outer compression surfaces and a plurality of concave portions, wherein each concave portion is positioned between a pair of respective outer compression surfaces. In some examples, at least one of the plurality of fibers is seated within one of the concave portions when the flexible body is in an unlocked state. In some examples, at least one of the plurality of fibers is compressed between one of the outer compression surfaces and an inner surface of the outer housing when the flexible body is in a locked state. In some examples, a single fiber, such as a single cable, may be locked in position to fix a flexible body into a particular shape.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

The invention claimed is:

1. A medical apparatus for bone fixation, the apparatus comprising:
   a flexible body including:

a bone-engagement feature;
a plurality of fibers, each extending through the flexible body and each movable in an axial direction relative to at least one other of the plurality of fibers; and
a shape-locking section including a housing having a surface and a compression member, the shape-locking section being configured to lock the flexible body by compressing the plurality of fibers between the compression member and the surface of the housing, wherein,
the compression member includes a plurality of compression surfaces and a plurality of concave portions alternating with the plurality of compression surfaces; and
the shape-locking section is configured to unlock the flexible body by aligning each of the plurality of concave portions with a respective one of the plurality of fibers.

2. The medical apparatus of claim 1, wherein the shape-locking section is configured to lock the flexible body in a curved shape.

3. The medical apparatus of claim 1, wherein the plurality of fibers are:
mechanically fixed at a distal end of the flexible body; and
configured to move freely within the shape-locking section while the flexible body is unlocked.

4. The medical apparatus of claim 1, wherein the compression member is disposed, and is rotatable, within the housing.

5. The medical apparatus of claim 1, wherein the shape-locking section is positioned substantially at a proximal end of the flexible body.

6. The medical apparatus of claim 1, wherein the surface includes an inner surface of the housing.

7. The medical apparatus of claim 1, wherein the shape-locking section is configured to lock the flexible body in a shape of a curved cavity that is formed in, and that spans a fracture of, a bone.

8. The medical apparatus of claim 1, the shape-locking section is configured to lock the flexible body in a curved shape.

9. The medical apparatus of claim 1 wherein the flexible body is more rigid while locked than while unlocked.

10. A medical apparatus for bone fixation, the apparatus comprising:
a flexible body including:
a bone-engagement feature;
a plurality of fibers, each extending through the flexible body and each movable in an axial direction relative to at least one other of the plurality of fibers; and
a shape-locking section including a housing having a surface and a compression member, the shape-locking section configured to lock the flexible body by the surface of the housing, wherein:
the compression member includes a plurality of compression surfaces; and a plurality of the concave portions alternating with the compression surfaces, and
the shape-locking section is configured to lock the flexible body by compressing each of the plurality of fibers against the surface of the housing with a respective one of the plurality of compression surfaces.

11. A medical apparatus for bone fixation, the apparatus comprising:
a flexible body including:
a proximal end,
a distal end, and
a plurality of lumens extending between the proximal and distal ends;
a bone-engagement feature positioned substantially at the distal end;
a plurality of fibers each extending through a respective one of the plurality of lumens; and
a shape-locking section including a housing having a surface and a compression member having a plurality of compression surfaces and a plurality of concave portions alternating with the plurality of compression surfaces, the shape-locking section being configured to lock the flexible body by causing each of the plurality of compression surfaces to compress a respective one of the plurality of fibers against the surface of the housing.

12. The medical apparatus of claim 11, wherein the compression member is configured to rotate within the housing.

13. The medical apparatus of claim 11, wherein the compression member comprises a cam having a plurality of compression surfaces and a plurality of concave portions each positioned between a respective pair of the plurality of compression surfaces.

14. The medical apparatus of claim 13, wherein the shape-locking section is configured to unlock the flexible body by causing each of the plurality of fibers to seat within a respective one of the plurality of concave portions.

15. The medical apparatus of claim 13, wherein the shape-locking section is configured to lock the flexible body by causing the compression member to compress each of the plurality of fibers between a respective one of the plurality of compression surfaces and the surface of the housing.

16. The medical apparatus of claim 11, wherein the shape-locking section extends from the proximal end of the flexible body.

17. The medical apparatus of claim 11, wherein the surface includes an inner surface of the housing.

18. A medical apparatus for bone fixation, the apparatus comprising:
a flexible body including:
a bone-engagement feature;
a plurality of fibers, each extending through the flexible body and each movable in an axial direction relative to at least one other of the plurality of fibers; and
a shape-locking section including a housing having a surface and a compression member, the shape-locking section being configured to lock the flexible body by compressing the plurality of fibers between the compression member and the surface of the housing, wherein the shape-locking section is configured to unlock the flexible body by allowing the plurality of fibers to slide between the compression member and the surface of the housing.

19. The medical apparatus of claim 18, wherein the compression member is disposed, and is rotatable, within the housing.

20. The medical apparatus of claim 18, wherein the shape-locking section is positioned substantially at a proximal end of the flexible body.

21. The medical apparatus of claim 18, wherein the surface includes an inner surface of the housing.

22. The medical apparatus of claim 18, wherein the shape-locking section is configured to lock the flexible body in a shape of a curved cavity that is formed in, and that spans a fracture of, a bone.

23. The medical apparatus of claim 18, the shape-locking section is configured to lock the flexible body in a curved shape.

24. The medical apparatus of claim 18 wherein the flexible body is more rigid while locked than while unlocked.

25. The medical apparatus of claim 18, wherein the shape-locking section is configured to lock the flexible body in a curved shape.

26. The medical apparatus of claim 18, wherein the plurality of fibers are:
- mechanically fixed at a distal end of the flexible body; and
- configured to move freely within the shape-locking section while the flexible body is unlocked.

* * * * *

UNITED STATES PATENT AND TRADEMARK OFFICE
CERTIFICATE OF CORRECTION

PATENT NO. : 11,419,645 B2
APPLICATION NO. : 16/340067
DATED : August 23, 2022
INVENTOR(S) : Stinson et al.

Page 1 of 1

It is certified that error appears in the above-identified patent and that said Letters Patent is hereby corrected as shown below:

On the Title Page

Item (60), in Column 1, under "Related U.S. Application Data", Line 1, delete "62/406,658," and insert -- 62/404,658, --, therefor.

In the Claims

In Column 19, in Claim 10, Lines 53-54, delete "body by the" and insert -- body by compressing the plurality of fibers between the compression member and the --, therefor.

In Column 19, in Claim 10, Line 56, delete "surfaces;" and insert -- surfaces --, therefor.

Signed and Sealed this
Twenty-fifth Day of October, 2022

Katherine Kelly Vidal
*Director of the United States Patent and Trademark Office*